(12) United States Patent
Karnik et al.

(10) Patent No.: US 9,555,413 B2
(45) Date of Patent: Jan. 31, 2017

(54) CELL ROLLING SEPARATION

(71) Applicant: Massachusetts Institute of Technology, Cambridge, MA (US)

(72) Inventors: Rohit Nandkumar Karnik, Cambridge, MA (US); Seungpyo Hong, Naperville, IL (US); Ying Mei, Cambridge, MA (US); Daniel Griffith Anderson, Sudbury, MA (US); Jeffrey Michael Karp, Brookline, MA (US); Robert S. Langer, Newton, MA (US); Suman Bose, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 3 days.

(21) Appl. No.: 14/667,615

(22) Filed: Mar. 24, 2015

(65) Prior Publication Data

US 2015/0246354 A1 Sep. 3, 2015

Related U.S. Application Data

(62) Division of application No. 12/680,249, filed on Jun. 22, 2010, now Pat. No. 8,986,988.

(60) Provisional application No. 60/975,813, filed on Sep. 27, 2007.

(51) Int. Cl.
| | |
|---|---|
| B01L 3/00 | (2006.01) |
| C12N 5/00 | (2006.01) |
| C12M 3/06 | (2006.01) |
| C12M 1/00 | (2006.01) |

(52) U.S. Cl.
CPC .... B01L 3/502761 (2013.01); B01L 3/502715 (2013.01); C12M 23/16 (2013.01); C12M 47/02 (2013.01); C12N 5/0068 (2013.01); B01L 2200/0647 (2013.01); B01L 2300/0877 (2013.01); B01L 2300/16 (2013.01); C12N 2501/58 (2013.01); C12N 2501/585 (2013.01); C12N 2533/50 (2013.01); C12N 2533/52 (2013.01); C12N 2535/10 (2013.01)

(58) Field of Classification Search
None
See application file for complete search history.

(56) References Cited

U.S. PATENT DOCUMENTS

| | | |
|---|---|---|
| 2004/0241168 A1 | 12/2004 | O'Daly |
| 2006/0177815 A1 | 8/2006 | Soh et al. |
| 2006/0183223 A1 | 8/2006 | King et al. |
| 2007/0178084 A1 | 8/2007 | King et al. |
| 2010/0112026 A1 | 5/2010 | Karp et al. |
| 2010/0304485 A1 | 12/2010 | Karnik et al. |
| 2011/0014600 A1 | 1/2011 | Oh et al. |

FOREIGN PATENT DOCUMENTS

| | | |
|---|---|---|
| JP | 09216902 A2 | 8/1997 |
| JP | 2009144928 A1 | 3/2009 |
| WO | 9801140 A1 | 1/1998 |
| WO | 2004075855 A2 | 9/2004 |
| WO | 2006068720 A2 | 6/2006 |
| WO | 2006078994 A2 | 7/2006 |
| WO | 2008070659 A1 | 6/2008 |
| WO | 2008089270 A2 | 7/2008 |
| WO | 2008131301 A1 | 10/2008 |

OTHER PUBLICATIONS

International Search Report for PCT/US2012/058375, dated Dec. 18, 2012 (3 pages).
Extended European Search Report for EP 08746368.3, pp. 1-7 (Nov. 9, 2010).
Hong, Seungoyo, et al. "Covalent Immobilization of P-Selection Enhances Cell Rolling", The ACS Journal of Surfaces and Colloids: vol. 23. Nr. 24, pp. 12261-12268, (Nov. 20. 2007).
Nafayancle, Divya D., et al. "Micropatterned Surfaces for Controlling Cell Adhesion and Foiling Under Flow", Biomedical Microdevices, vol. 9, No. 2, pp. 207-214 (Apr. 1, 2007).
Tang, J. et al. "Dynamics of in Silico Leukocyte Rolling, Activation, and Adhesion", BMC Syst Biol. 1:14, (Feb. 19, 2007).
Buftrum SM. "Selectin-Mediated Rolling of Neutrophils on Immobiiized Platelets", Blood, 82(4), pp: 1165-1174 (Aug. 14. 1993).
Schon MP "Inhibitors of Selectin Functions in the Treatment of Inflammatory Skin Disorders", Ther Clin Risk Manag., 1(3). pp. 201-208 (Sep. 2005).
International Search Report for PCT/US2008/060934, mailed Aug. 25, 2008.
Written Opinion for PCT/US2008/060934, mailed Aug. 25, 2008.
Rusmini, et al. "Protein immobilization Strategies for Protein Biochips", Biornacromoleoules, 8(6): pp. 1176-1789 (Jun. 2007).
Leckband, et al. "An Approach for the Stable Immobilization of Proteins", Biotechnology and Bioengineering, 37(3): pp. 227-237 (1991).
Gregorius, et al. "Analytical Biochemistry", 299(1): pp. 84-91 (Dec. 1, 2001).
Gout, S. et al. "Selectins and Selectin Ligands In Extravasation of Cancer Cells and Organ Selectivity of Metastasis". Clinical and Experimental Metastasis (2007).
King, M.R. "Scale Invariance in Selectin-Mediated Leukocyte Rolling". Fractals—Complex Geometry Patterns and Scaling in Nature and Society: 12, pp. 235-241 (2004).
King, M.R. et al. "Rolling Dynamics of a Neutrophil With Redistributed L-Selectin", Mathematical Biosciences: 194, pp. 71-79 (2005).
King, M.R., et al. "Multiparticle Adhesive Dynamics: Hydrodynamic Recruitment of Rolling Leukocytes", Proceedings of the National Academy of Sciences of the United States of America: 98, pp. 14919-14924 (2001).
Gordon, M.Y. et al. "Contact-Mediated Inhibition of Human Haematopoietic Progenitor Cell Proliferatio May Be Conferred by Stem Cell Antigen, CD-34", Hernatol J: 1, pp. 77-86 (2000).

(Continued)

*Primary Examiner* — Antonio Galisteo Gonzalez
(74) *Attorney, Agent, or Firm* — Thomas J. Engellenner; Reza Mollaaghababa; Pepper Hamilton LLP

(57) ABSTRACT

The present invention provides systems for cell separation based on cell rolling on surfaces along edges of regions coated with cell adhesion molecules. A variety of designs of coated regions and edges are disclosed.

24 Claims, 19 Drawing Sheets

(56) References Cited

OTHER PUBLICATIONS

Lawrence, M.D., et al. "Leukocytes Roll on a Selectin at Physiologic Flow Rates: Distinction from and Prerequisite for Adhesion Through Integrins", Cell: 65, pp. 859-873 (1991).

Williams et al. "Fibronectin and VLA-4 in Haematopoietic Stem Cell-Microenvironment Interactions", Nature. vol. 352, pp. 438-441 (Aug. 1, 1991).

Dong et al. "Biomechanics of Cell Rolling: Shear Flow, Cell-Surface Adhesion and Cell Deformability", Journal of Biomecahnics, vol. 33, pp. 35-43 (2000).

Chang et al. "Biomimetic Technique for Adhesion-Based Collection and Separation of Cells in a Microfluidic Channel", 20 Lab Chip. vol, 5; pp. 64-73 (2005).

Goldman et al. "Slow Viscous Motion of a Sphere Parallel to a Plane Wall ll Coulette Flow", Chemical Engineering Science, 22, pp. 653-660 (1967).

Delamarche, E., et al. "Patterned Delivery of Immunogiodulins to Surfaces Using Microfluidic Networks", Science, 276 (5313): pp. 779-780 (1997).

Dimitroff, C.J., et al. "CD44 is a Major E-Selectin Ligand on Human Hematopoietic Progenitor Cells", Journal of Cell Biology, 153(6): pp. 1277-1266 (2001).

Pittenger, M.F. "Multilineage Potential of Adult Human Mesenchymal Stem Cells":, Science. 284(5411): pp. 143-147 (1999).

Caplan, A.I. "Mesenchymal Stem Cells", J Orthp Res., 9(5): pp. 641-650 (1991).

Mrksich, M., et al. "Controlling Cell Attachment on Contoured Surfaces With Self-Assembled Monolayers of Alkanethiolates on Gold", Proceedings of the National Academy of Sciences of the United States of America, 93(20): pp. 10775-10778 (1996).

Fujimoto, T., et al. "P-Selectin is Acylated With Palmitic Acid and Stearic Acid At Cystein-766 Through a Thioester Linkage", Journal of Biological Chemistry, 268(15): pp. 11394-11400 (1993).

Dong, C., et al. "Biomechanics of Cell Rolling: Shear FLow, Cell-Surface Adhedsion, and Cell Deformability", 33(1): pp. 35-43 (2000).

Davies, J.E., et al. "Desposition and Resorption of Calcified Matrix In Vitro by Rant Marow Cells", Cells and Materials, 1(1) pp. 3-15 (1991).

Baksh, D., et al. "Adult Human Bone Marrow-Derived Mesenchymal Progenitor Cells Are Capable of Adhesion-Independent Survival and Expansion", Exp. Hematol; 31(8): pp. 723-732 (2003).

Karp et al. "Thrombin Mediated Migration of Osteogenic Cells" Bone, 37 pp. 337-348 (2005).

Castro-Malaspina et al. "Characterization of Human Bone Marrow Fibroblast Colony-Forming Cells (CFU-F.) and Their Progeny", Blood, 56(2) pp. 289-301 (1980).

Bbandari, V., et al. "Hematologic Profile of Sepsis in Neonates: Nutrophil CD64 as a Diagnostic Marker", 121(1); pp. 129-134 (2008).

Ng, P. "Neutrophil CD64 Expression: A Sensitive Diagnostic Marker for Late-Onset Nosocomial Infection in Very Low Birthweight Infants", Pediatric Research, 2002: 51(3): pp. 296-303 (2002).

Duffy, D.C. et al. Rapid Prototyping of Microfluidic Systems in Poly(Dirrethylsiloxane):, Analytical Chemistry, 70(23): pp. 4974-4984 (1998).

Hong, S., et al. "Covalent Immobiiization of P-Selectin Enhances Cell Rolling", Langmuir, 23(24) pp. 12261-12268 (2007).

Davis, B.H. et al.; "Neutrophil CD64 is an Improved Indicator of infection of Sepsis in Emergency Department Patients", Archives of Pathology & Laboratory Medicine, 130(5) pp. 654-661 (2006).

Thorsen, T., et al., "Microfiuidic Large-Scale Integration", Science, 298(5593), pp. 580-584 (2002).

Nagrath, S. et al. "Isolation of Rare Circulating Tumor Cells in Cancer Patient by Microchip Technology", Nature. 450 (7173). pp. 1235-U10 (2007).

International Search Report for PCT/US2008/078204, mailed May 26, 2009.

Written Opinion for PCT/US2008/078204, mailed May 26, 2009.

Greenberg, A.W., et al. "Cell Separation Mediated by Differential Rolling Adhesion", Biotechnol. Bioeng., vol. 74, pp. 111-124 (2001).

Karnik, R., et al. "Namomechanical Control of Cell Rolling in Two Dimensions Through Surface Pattering of Receptors" Nano Letters, 8(4), pp. 1153-1158.

Extended European Search Report for 08834284.5, pp. 7 (Dec. 6, 2011).

Mateo et al. "Increase in Conformational Stability of Enzymes Immobilized on Epoxy-Activated Supports by Favoring Additional Multipoint Covalent Attachment", Enzyme Microb Technol., 26(7) pp. 509-515 (Apr. 1, 2000).

Kusnezow et al. "Antibody Mioroarrays: An Evaluation of Production Parameters" Protemics, 3, pp. 254-264 (2003).

Uchiyama et al., "Development of a Lectin Microarray Based on an Evanescent-field Fluorescence Principle", Methods Enzymol. 415, pp. 341-351 (2006).

Karp et al., "Cultivation of Human Embryonic Stem Cells Without the Embryoid Body Step Enhances Osteogenesis in Vitro", Stem Cells, 24 pp. 835-843 (2006).

Willams et al, "Fibronectin and VLA-4 in Haematopoietic Stem Cell-Microenvironment Interactions", pp. 438-441 (Aug. 1, 1991).

Lee et al. "Examining the Lateral Displacement of HL60 Cells Rolling on Asymmetric P-Selection Patterns", Langmuir, vol. 27, Iss. 1 pp. 240-249 (Jan. 4, 2011).

CELL ROLLING SEPARATION

RELATED APPLICATION INFORMATION

The present application is a divisional of U.S. patent application Ser. No. 12/680,249, filed Jun. 22, 2010, that claims benefit to Provisional Application No. 60/975,813, filed Sep. 27, 2007. This application also claims priority to International Application No. PCT/US2008/078204, filed Sep. 29, 2008. Each of these applications is herein incorporated by reference in its entirety.

GOVERNMENT RIGHTS

This invention was made with U.S. government support under Grant Nos. R01DE016516 awarded by National Institutes of Health. The U.S. government has certain rights in the invention.

BACKGROUND

Cell rolling is an important physiological and pathological process that is used to recruit specific cells in the bloodstream to a target tissue. For example, cell rolling along vascular endothelium in viscous shear flow is of primary biological importance, given its role in recruitment of leukocytes to sites of inflammation, homing of hematopoietic progenitor cells after intravenous injection, tumor cell metastasis and other inflammatory processes.

Cell rolling is a receptor-ligand mediated event that initiates an adhesion process to a target tissue through a reduction in cell velocity. Cell rolling is typically followed by activation, firm adhesion, and transmigration. The rolling response is primarily mediated by a family of transmembrane glycoprotein receptors called selectins, which are expressed on the surfaces of leukocytes and activated endothelial cells. Selectins bind to carbohydrates via a lectin-like extracellular domain. The broad family of selectins is divided into L-selectin (CD62L), E-selectin (CD62E), and P-selectin (CD62P). L-selectin (74-100 kDa) is found on most leukocytes and can be rapidly shed from the cell surface. E-selectin (100 kDa) is transiently expressed on vascular endothelial cells in response to IL-1 beta and TNF-alpha. P-selectin (140 kDa) is typically stored in secretory granules of platelets and endothelial cells.

For example, the adhesion mechanism that mediates leukocyte rolling on the vascular endothelium is often referred to as cell rolling. This mechanism involves the weak affinity between P-selectin and E-selectin (expressed on vascular endothelial cells) and selectin-binding carbohydrate ligands (expressed on circulating hematopoietic stem cells (HSC) and leukocytes). Once 'captured', cells roll slowly over the surface, in contrast to uncaptured cells, which flow rapidly in the bulk fluid.

SUMMARY

The present invention encompasses the finding that the direction of motion of rolling cells can be altered by altering the arrangement of molecules on surfaces on which cells roll. In particular, we have demonstrated that cells may be diverted from the direction of flow using an edge between a region coated with molecules that facilitate cell rolling and an uncoated area (e.g., see FIG. 1C). In certain embodiments, a stagnation line of no flow may act in lieu of or in addition to such an edge to facilitate cell rolling at an angle to the direction of flow.

The inventions described herein take advantage of these findings to provide systems for cell rolling-based separation. Separated cells may be used for any purpose, including without limitation diagnostic or therapeutic purposes.

In some aspects, methods are provided that may be useful for cell separation applications.

In certain embodiments, methods comprise providing a surface that is at least partially coated with an ordered layer of cell adhesion molecules, wherein the surface comprises at least one edge between an area coated with the ordered layer and another area that is not coated with the ordered layer, and flowing a population of cells across the surface in a direction which forms a non-zero angle $\alpha_s$ with the at least one edge. In such methods, at least one cell in the population of cells comprises a surface moiety that is recognized by the cell adhesion molecules and at least one cell in the population of cells rolls for a period of time in a direction that is $\alpha$ to the direction of flow as a result of interacting with at least a portion of the at least one edge.

In certain embodiments, methods comprise providing a three dimensional surface that is at least partially coated with an ordered layer of cell adhesion molecules, and flowing a population of cells across the surface in such conditions to create a stagnation line of no flow. In such embodiments, the direction of flow forms a non-zero angle $\alpha_s$ with the stagnation line, at least one cell in the population of cells comprises a surface moiety that is recognized by the cell adhesion molecules, and at least one cell in the population of cells rolls at least part of the time in a direction that is $\alpha_s$ to the direction of flow.

In some aspects, provided are devices for cell separation comprising a separation flow chamber, an inlet for flowing cells into the separation flow chamber, and an outlet for flowing cells out of the separation flow chamber. In such devices, the separation flow chamber comprises a surface that is at least partially coated with an ordered layer of cell adhesion molecules, wherein the surface comprises at least one edge between an area coated with the ordered layer and another area that is not coated with the ordered layer. In such devices, when cells are flowed through the inlet to the outlet, they flow at an angle $\alpha_s$ to the direction of the at least one edge.

DEFINITIONS

Figure 1:
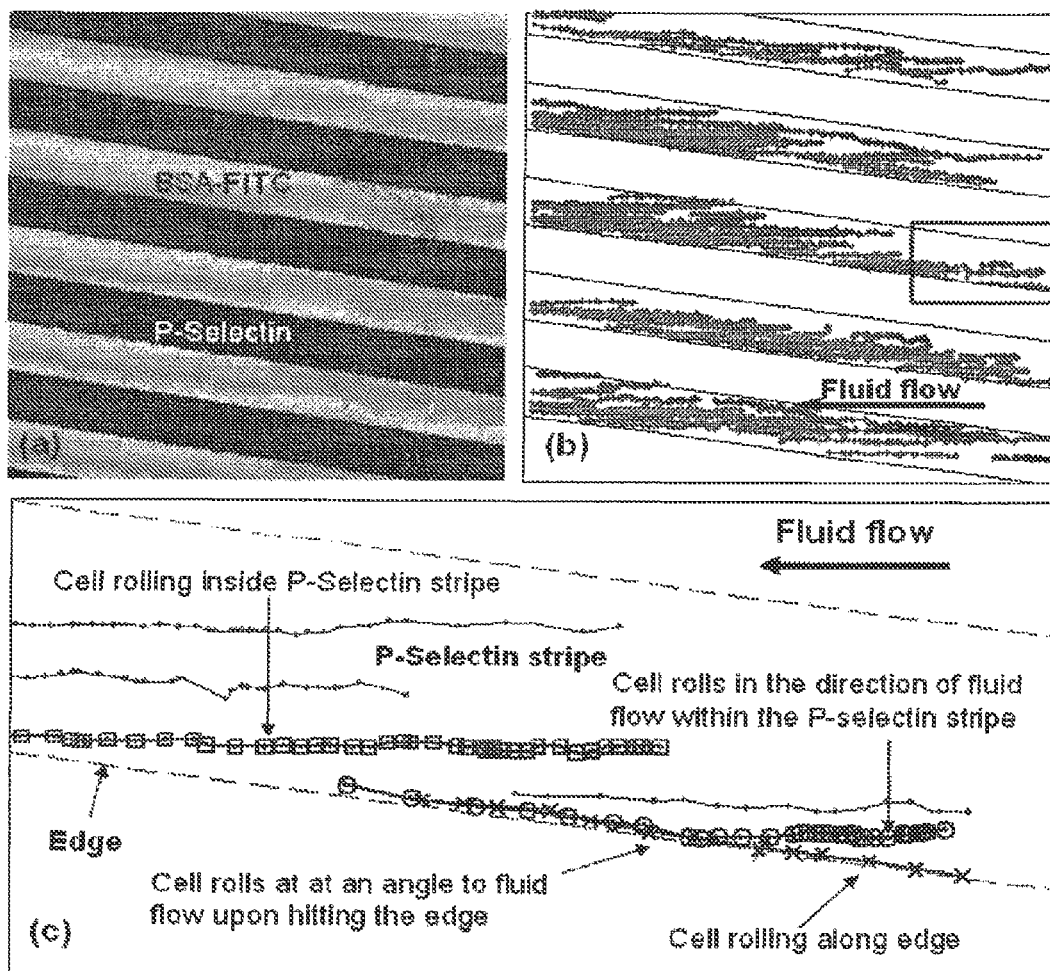
FIG. 1 shows (A) P-Selectin immobilized on a polystyrene substrate using microfluidic technology to create edges followed by adsorption of BSA-FITC to reveal the design. Stripes were 100 µm wide. (B) Tracks of rolling HL-60 cells which were flowed at concentration of $1\times10^6$ cells/mL over the substrate at a shear rate of 2 dyn/cm$^2$. Tracks were obtained by processing 194 images acquired at 0.5 Hz using a Matlab code. Cells can be seen to interact and roll only on the selectin stripe. (C) A magnified image of the inset showing representative tracks reveals that cells roll in the direction of fluid flow within the P-selectin stripe, but change direction and roll along the edge upon encountering the edge (marker O). Cells within the P-Selectin stripe that do not encounter the edge (marker □) roll in the direction of the fluid flow, and not in the direction of the stripe. Other cells can be seen rolling on the edge (marker x). The direction of cell rolling is determined by the edge, and not by the shape of the coated area on which the cells roll.

Throughout the specification, several terms are employed that are defined in the following paragraphs.

The terms "about" and "approximately," as used herein in reference to a number, generally includes numbers that fall within a range of 5%, 10%, or 20% in either direction of the number (greater than or less than the number) unless otherwise stated or otherwise evident from the context (except where such number would exceed 100% of a possible value).

The phrase "adhesive patch" as used herein refers to a region (such as, for example, on a surface) onto which molecules to which cells can adhere are arranged. Such adhesive molecules generally can comprise any ligands with stronger interactions with cells than cell adhesion molecules. Examples of such molecules include antibodies and antibody fragments. The density of such molecules in the adhesive patch (or the dimensions of the patch) may in some embodiments be controlled such that cells encountering the patch slow down but do not stop. In some embodiments, the density of molecules in the adhesive patch (or the dimensions of the patch) is controlled such that cells encountering the patch stop.

The term "adsorb" is used herein consistently with its generally accepted meaning in the art, that is, to mean "to collect by adsorption." "Adsorption" refers to the process by which specific gasses, liquids or substances in solution adhere to exposed surfaces of materials, usually solids, with which they are in contact.

The term "cell adhesion molecule," as used herein, generally refers to proteins located on cell surfaces involved in binding (via cell adhesion) of the cell on which it is found with other cells or with the extracellular matrix. Examples of cell adhesion molecules include, but are not limited to, full-length, fragments of, analogs of, and/or modifications of selectins (e.g., E-selectins, P-selectins, L-selectins, etc.), integrins (e.g., ITGA4, etc.), cadherins (e.g., E-cadherins, N-cadherins, P-cadherins, etc.), immunoglobulin cell adhesion molecules, neural cell adhesion molecules, intracellular adhesion molecules, vascular cell adhesion molecules, platelet-endothelial cell adhesion molecules, L1 cell adhesion molecules, and extracellular matrix cell adhesion molecules (e.g., vitronectins, fibronectins, laminins, etc.). As used herein, the term "cell adhesion molecule" also encompasses other compounds that can facilitate cell adhesion due to their adhesive properties. In some embodiments of the invention, aptamers, carbohydrates, peptides (e.g., RGD (arginine-glycine-aspartate) peptides, etc.), and/or folic acid, etc. can serve as cell adhesion molecules. As used herein, such compounds are encompassed by the term "cell adhesion molecule." As used herein, terms referring to cell adhesion molecules including, but not limited to, "cell adhesion molecule," "selectin," "integrin," "cadherin," "immunoglobulin cell adhesion molecule," "neural cell adhesion molecules," "intracellular adhesion molecules," "vascular cell adhesion molecules," "platelet-endothelial cell adhesion molecules," "L1 cell adhesion molecules," "extracellular matrix cell adhesion molecules," encompass full length versions of such proteins as well as functional fragments, analogs, and modifications thereof, unless otherwise stated. Likewise, terms referring to specific cell adhesion molecules including, but not limited to, "E-selectin," "P-selectin," "L-selectin," "ITGA4," "E-cadherin," "N-cadherin," "P-cadherin," "vitronectin," "fibronectin," "laminin," etc., also encompass full length versions of such proteins as well as functional fragments, analogs, and modifications thereof, unless otherwise stated. As used herein, the term "cell adhesion molecule" does not encompass antibodies.

The phrase "cell culture," is used herein to refer to the growing of cells, typically in a controlled environment. Such cells can be derived from multicellular eukaryotes, especially animal cells, or can be microorganisms such as bacteria. The term "tissue culture" is often used interchangeably with the term "cell culture" when the cells are derived from multicellular eukaryotic animals.

The term "cell modifying ligand," as used herein, generally refers to molecules that are capable of modifying the biological behavior of a cell. For example, a protein that triggers a molecular signal within a cell (e.g., expression of another protein) is a cell modifying ligand.

The term "deformability," as used herein, where it refers to cells, means the ability of cells to change their shape, such as, for example, as they pass through narrow spaces, as they roll along a surface, etc.

The term "linker," as used herein, refers to a chemical moiety used to attach a group or moiety (e.g., a cell adhesion molecule) to another functional group (such as, for example, a functional group immobilized on a surface). Without limitation, in some embodiments, the linker moiety comprises one or more of a dextran, a dendrimer, polyethylene glycol (PEG), poly(L-lysine), poly(L-glutamic acid), poly (D-lysine), poly(D-glutamic acid), polyvinyl alcohol, and polyethylenimine. In some embodiments, the linker moiety comprises one or more of an amine, an aldehyde, an epoxy group, a vinyl, a thiol, a carboxylate, and a hydroxyl group. In some embodiments, the linker moiety includes a member of a ligand/receptor pair and the cell surface molecule has been chemically modified to include the other member of the pair.

The phrase "mesenchymal stem/progenitor cell" (abbreviated "MSPC"), as used herein, refers to self-renewing and multipotent cells that are distributed in a variety of adult and fetal tissues including the bone marrow, skin, kidney, lung and liver. MSPCs can be maintained and propagated in culture prior to directing the differentiation into multiple cell types including adipocytes, chondrocytes, osteoblasts, hepatocytes, and cardiomyocytes. Bone marrow and adipose tissue are the most abundant sources of MSPCs. The phrase is used interchangeably with "mesenchymal stem cell" (abbreviated "MSC").

The term "oriented," as used herein, is used to describe molecules (e.g., cell adhesion molecules, etc.) having a definite or specified spatial orientation, that is, a non-random orientation. For example, cell adhesion molecules are "oriented" on a surface if a substantial portion of the cell adhesion molecules on the surface have a particular spatial orientation with respect to the surface. In certain embodiments of the invention, the "substantial portion" comprises at least 50% of the molecules on the surface.

The term "unoriented," as used herein, is used to describe molecules (e.g., cell adhesion molecules, etc.) having no particular or specified orientation, that is, a random orientation. For example, cell adhesion molecules may be described as "unoriented" on a surface if the cell adhesion molecules generally do not have a defined orientation with respect to the surface.

The term "ordered layer," as used herein, refers to a layer having a property which is substantially uniform, periodic, and/or patternwise over at least 50% of the layer. In some embodiments, an ordered layer has one or more features chosen from a substantially uniform density and a substantially uniform spatial orientation of the cell adhesion molecules. In some embodiments, an ordered layer has one or more features chosen from a patternwise distribution, a patternwise density, and a patternwise spatial orientation of the cell adhesion molecules. In some embodiments, the ordered layer of cell adhesion molecules allows a velocity of cell rolling over the ordered layer that is substantially proportional to the shear stress applied to the ordered layer.

The term "physisorb" is used herein consistently with its generally accepted meaning in the art, that is, "to collect by physisorption." "Physisorption" refers to adsorption that does not involve the formation of chemical bonds.

The phrase "progenitor cell" as used herein refers to cells that have a capacity to differentiate into a specific type of cell. The term generally refers to cells that are further differentiated along a particular lineage than stem cells.

The term "self-assembled monolayer" (abbreviated as "SAM"), as used herein, refers to a surface comprising a single layer of molecules on a substrate that can be prepared by adding a solution of the desired molecule onto the substrate surface and washing off the excess.

The phrase "stagnation line," as used herein, refers to a region of zero flow velocity near a surface of an object where flows on the surface converge from different directions. The shear along the stagnation line is zero, and the flow velocity close to the surface defines a plane passing through the stagnation line. In this plane, the flow velocity must make an angle other than 90 degrees with respect to the stagnation line. (The angle is 90 degrees in the case of vertical posts).

The phrase "stem cell" as used herein refers to cells that are capable of self renewal through mitotic cell division and are capable of differentiating into a diverse range of specialized cell types. Examples of stem cells include, but are not limited to, mesenchymal stem cells, hematopoietic stem cells, and embryonic stem cells.

DETAILED DESCRIPTION OF CERTAIN EMBODIMENTS

As mentioned above, the present invention provides systems useful for cell separation by employing cell rolling across a surface.

I. Methods

Provided are methods comprising steps of providing a surface at least partially coated with an ordered layer of cell adhesion molecules and flowing a population of cells across the surface. Surfaces comprise at least one edge between an area coated with the ordered layer and an area that is not coated with the ordered layer. Populations of cells are flowed across surfaces in a direction that together with at least one edge form a non-zero angle $\alpha_s$. At least one cell in the population of cells comprises a surface moiety that is recognized by the cell adhesion molecules, and rolls at least part of the time in a direction $\alpha_s$ to the direction of flow as a result of interacting with the edge. In some embodiments, such cells roll along the edge at least part of the time.

In certain embodiments, methods further comprise separating the at least one cell from certain cells in the population. In some embodiments, cells comprising the surface moiety roll on the coated area, but at a distance which is at least one cell diameter away from the edge.

In such embodiments, the cells may roll at an angle which is smaller than $\alpha_s$. In some such embodiments, the angle smaller than $\alpha_s$ is or approximates zero. That is, cells that do not interact with the at least one edge roll in the direction of flow.

A. Coated Surfaces

Surfaces are generally partially coated with an ordered layer of cell adhesion molecules and may or may not comprise additional molecules as discussed herein.

Cell Adhesion Molecules

A variety of cell adhesion molecules can be used in the practice of certain embodiments of the present invention. In some embodiments, the layer of cell adhesion molecules comprises cell adhesion molecules having a dissociation constant ($K_D$) for interaction with one or more cell surface moieties (e.g., proteins, glycans, etc.) that is greater than about $1 \times 10^{-8}$ mole/liter (M). In some embodiments, the layer of cell adhesion molecules comprises cell adhesion molecules having a dissociation constant ($K_D$) for interaction with one or more cell surface moieties that is in the range of about $1 \times 10^{-4}$ molar to about $1 \times 10^{-7}$ M, inclusive. It will be appreciated that the behavior of cells on the coated surface will depend in part on the dissociation constant.

In general, any cell adhesion molecule may be used. Examples of cell adhesion molecules useful in certain embodiments of the present invention include, but are not limited to, full-length, fragments of, analogs of, and/or modifications of selectins (e.g., E-selectins, P-selectins, L-selectins, etc.), integrins (e.g., ITGA4, etc.), cadherins (e.g., E-cadherins, N-cadherins, P-cadherins, etc.), immunoglobulin cell adhesion molecules, neural cell adhesion molecules, intracellular adhesion molecules, vascular cell adhesion molecules, platelet-endothelial cell adhesion molecules, L1 cell adhesion molecules, and extracellular matrix cell adhesion molecules (e.g., vitronectins, fibronectins, laminins, etc.). In some embodiments, aptamers, carbohydrates, peptides (e.g., an RGD peptide), folic acid, etc. can serve as cell adhesion molecules. The layer of cell adhesion molecules may include a single cell adhesion molecule or a combination of different kinds of cell adhesion molecules.

Cell adhesion molecules may be bound to surfaces in a variety of ways. Noncovalent interactions such as, for example, van der Waals interactions, hydrogen bonding, and electrostatic interactions (also known as ionic bonding) etc. may be used.

Covalent bonds may also be used. Any covalent chemistry may be used to covalently attach cell adhesion molecules to a substrate surface. Those skilled in the art will appreciate that the methods described in the Examples are exemplary and could be readily modified based on knowledge in the art. In some embodiments, cell adhesion molecules are attached to a surface through one or more linker moieties. In some embodiments, a linker moiety is bound to the cell adhesion molecule at one of its ends and to the surface of the substrate at another end. In general, the bond between the linker moiety and the surface is covalent. The bond between the linker moiety and the cell adhesion molecule may be covalent or non-covalent (e.g., if it involves a ligand/receptor pair as discussed herein). Without limitation, in some embodiments, the linker moiety comprises one or more of a dextran, a dendrimer, polyethylene glycol (PEG), poly(L-lysine), poly(L-glutamic acid), poly(D-lysine), poly(D-glutamic acid), polyvinyl alcohol, and polyethylenimine. In some embodiments, the linker moiety comprises one or more of an amine, an aldehyde, an epoxy group, a vinyl, a thiol, a carboxylate, and a hydroxyl group. In some embodiments, the linker moiety includes a member of a ligand/receptor pair and the cell surface molecule has been chemically modified to include the other member of the pair.

In addition to improving the long term stability and behavior of the coated surface, the use of covalent bonding instead of physisorption, enables one to control the density, arrangement and orientation of cell adhesion molecules on the substrate surface. For example, the density will depend on the density of groups on the surface which are available for covalent bonding. Similarly, the arrangement will depend on the arrangement of groups on the surface which are available for covalent bonding. Methods are well known in the art for preparing surfaces with different densities and arrangements of suitable groups for covalent bonding (e.g., see Rusmini et al. Protein immobilization strategies for protein biochips. *Biomacromolecules* 2007 June; 8(6):1775-89. and Leckband et al. An approach for the stable immobilization of proteins. *Biotechnology and Bioengineering* 1991; 37(3):227-237, the entire contents of both of which are incorporated herein by reference). In some embodiments, the density of cell adhesion molecules ranges from about 10 ng/cm$^2$ to about 600 ng/cm$^2$. In some embodiments, the density of cell adhesion molecules is greater than about 30 ng/cm$^2$. For example, in some embodiments, the density of cell adhesion molecules ranges from about 30 ng/cm$^2$ to about 360 ng/cm$^2$. In some embodiments, the density of cell adhesion molecules ranges from about 50 ng/cm$^2$ to about 300 ng/cm$^2$. In some embodiments, the density of cell adhesion molecules ranges from about 100 ng/cm$^2$ to about 200 ng/cm$^2$.

In some embodiments, the orientation of cell adhesion molecules on the surface is controlled. This can be advantageous, e.g., because the cell adhesion molecules are forced to interact with cells only if a particular region of the cell adhesion molecules is accessible to the cells. For example, P-selectin includes a single cysteine residue. As a result, if P-selectin is attached to the surface via a linker moiety that reacts specifically with cysteine, all P-selection molecules will be attached to the surface with the same orientation. In general, this approach can be applied whenever the cell adhesion molecule includes a unique group. In some embodiments, a cell adhesion molecule can be engineered or chemically modified using methods known in the art to include such a unique group (e.g., a particular amino acid residue) at a position that provides an optimal orientation. For example, a suitable amino acid residue can be added at the C- or N-terminus of protein based cell adhesion molecules.

In some embodiments, the cell adhesion molecules are synthesized and/or purified such that only a limited subset of the residues is able to react with reactive groups on the surface or on the linker. In some embodiments, there is only one group or residue on each cell adhesion molecule that can react with reactive groups on the surface or on the linker. For example, in some embodiments, cell adhesion molecules are synthesized and/or purified with protecting groups that prevent the residues to which they are attached from reacting with reactive groups on the surface or linker. In such embodiments, one or more residues in the cell adhesion molecule are not protected. Because the cell adhesion molecule can only attach to the surface or linker via the one or more unprotected residues, the cell adhesion molecule may attach to the surface or linker in a specific orientation. In some embodiments, the protective groups are removed after attachment of the cell adhesion molecule to the surface or linker. (See, e.g., Gregorius et al. Analytical Biochemistry 2001 Dec. 1;299(1):84-91, the entire contents of which are incorporated herein by reference.)

Antibodies

In some embodiments, antibodies (including antibody fragments) may be co-immobilized with cell adhesion molecules. In general, an antibody may be attached to the surface in a similar fashion to the cell adhesion molecule (e.g., using the same linker moiety). In certain embodiments, the antibody may be attached using a different covalent attachment method. In certain embodiments, the antibody may be attached non-covalently. In certain embodiments, the ordered layer comprises at least one antibody that is covalently attached to the surface and least one antibody that is non-covalently attached to the surface.

In certain embodiments, an antibody that binds to a cell surface moiety may be coimmobilized with cell adhesion molecules. In principle, any pair of antibody and surface ligand may be used in accordance with the invention, so long as the antibody binds to the surface ligand. For example, if it is desired to modify interactions between the coated surface and a cell type that expresses CD64, anti-CD64 antibodies may be coimmobilized with cell adhesion molecules. Those skilled in the art will appreciate how this can be extended to other surface ligands that are known in the art. Molar ratios of cell adhesion molecules to antibodies in such embodiments may be varied depending on the desired rolling characteristics (such as, for example, velocity, percentage of cells stopping, etc.). Examples of suitable ratios include those ranging from about 100:1 to 1:100. In some embodiments, molar ratios range between 20:1 and 1:1.

In some embodiments, antibodies can be included in order to adjust the speed at which cells roll on a coated surface. In some embodiments this may be achieved by controlling the density and/or arrangement of antibodies. In some embodiments, antibodies may be immobilized onto surfaces at such a density as to slow down the speed of rolling without causing the cells to stop. In some embodiments, antibodies may be arranged onto surfaces at such a density as to cause cell rolling to stop.

Cell Modifying Ligands

In some embodiments, cell modifying ligands may be co-immobilized with cell adhesion molecules. In general, a cell modifying ligand may be attached to the surface in a similar fashion to the cell adhesion molecule (e.g., using the same linker moiety). In certain embodiments, the cell modifying ligand may be attached using a different covalent attachment method. In certain embodiments, the cell modifying ligand may be attached non-covalently. In certain embodiments, the ordered layer comprises at least one cell modifying ligand that is covalently attached to the surface and least one cell modifying ligand that is non-covalently attached to the surface.

In some embodiments, the population of cells which is flowed over a coated surface includes at least one subpopulation of cells with a common characteristic, and the cell modifying ligand is capable of modifying a phenotype of the subpopulation of cells. Any of a variety of cell types can comprise the subpopulation, as discussed herein. As an example, certain cancer cells may express a receptor such as TNF receptor 5 and/or 6, which is not expressed on normal cells. Tumor necrosis factor (TNF)-related receptor apoptosis-inducing ligand (TRAIL) specifically binds to TNF receptors 5 and 6. To induce apoptosis or programmed cell death of such cells, TRAIL may be co-immobilized with a cell adhesion molecule. Cell modifying ligands such as TRAIL and/or other chemotherapeutic agents can be co-immobilized with a cell adhesion molecule to impart signals to kill or arrest growth of cancer cells. It will be appreciated by those skilled in the art that other cell modifying ligands can be immobilized and/or presented on and/or within the substrate to influence the behavior of cells that interact with the cell adhesion molecules. For example, fibroblast growth factor 2 (FGF-2) can be presented to facilitate maintaining cells in an undifferentiated state. As a further example, bone morphogenic protein 2 (BMP-2) can be presented to stimulate osteogenic differentiation of stem cells, etc. Combinations of cell modifying ligands can also be used together.

B. Designs

In general, coated surfaces comprise at least one edge between a coated area and an uncoated area. The is no limitation on the types of designs which may be used in order to achieve one or more edges.

Edge(s)

At least one edge on the surface generally forms a non-zero angle $\alpha_s$ with the direction of flow. In certain embodiments, $\alpha_s$ is at least 0.5 degrees. $\alpha_s$ may be, in various embodiments, at least 1 degree, at least 2 degrees, at least 3 degrees, at least 4 degrees, at least 5 degrees, at least 6 degrees, at least 7 degrees, or at least 8 degrees. $\alpha_s$ may be, in various embodiments, less than about 70 degrees, less than about 65 degrees, less than about 60 degrees, less than about 55 degrees, less than about 50 degrees, less than about 45 degrees, less than about 40 degrees, less than about 35 degrees, less than about 30 degrees, less than about 25 degrees, less than about 20 degrees, or less than about 15 degrees.

Figure 2:
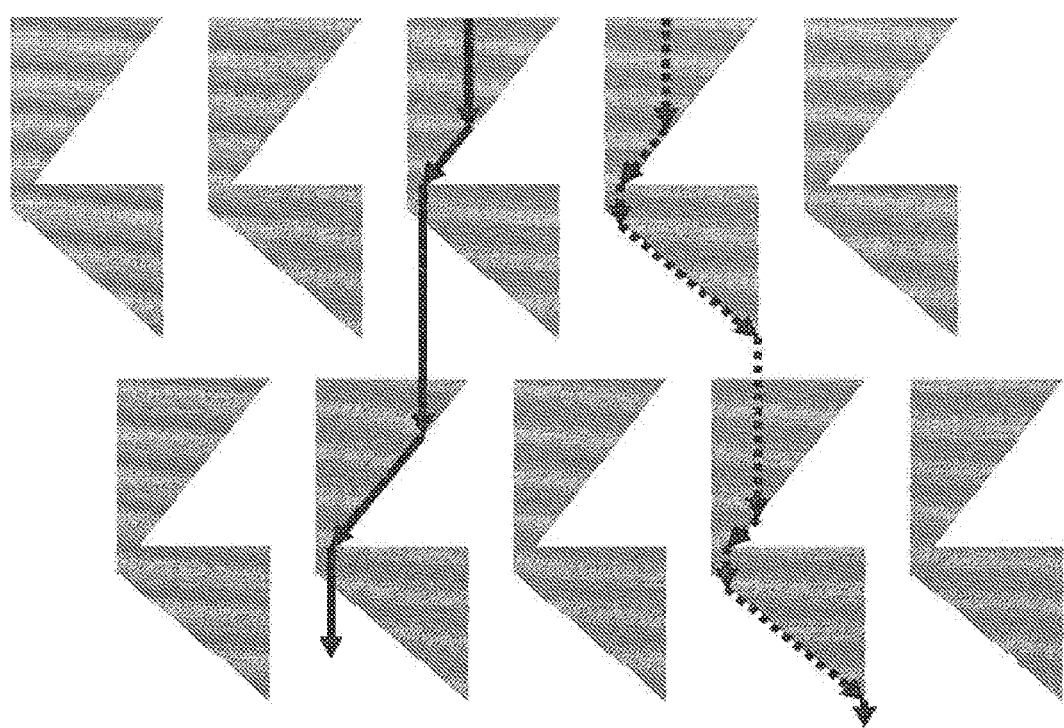
FIG. 2 depicts a schematic of an example of an edge design that would result in net displacements of two cell types in opposite directions. The surfaces comprises two different kinds of edges that make different angles with respect to the direction of flow. The first edge encountered by the cells makes an angle such that both cell types can follow it. The second edge is inclined at a larger angle or has receptors such that only one cell type (dashed line) can roll along that edge. A spatial variation in the above repeating design obtained by changing the second edge gradually over a large area can be used for focusing of a particular cell type.

The at least one edge may be substantially linear and/or may comprise a curved portion. In some embodiments, an edge may include both linear and curved portions. In some embodiments of the invention, surfaces comprise a plurality of edges. In some such embodiments of the invention, at least two of the edges form different angles to the direction of fluid flow. FIG. 2 shows one example of a design that makes use of plurality of edges having different angles.

In certain embodiments of the invention, the edge is a sharp edge. Sharpness of an edge may be characterized by a certain percent change in density over a given distance. When referring to edges between coated areas and uncoated areas, it may be useful to consider densities of molecules (e.g., cell adhesion molecules) in the ordered layer and use the maximum density in the coated area for comparison. "100% density" could be defined as the maximum density in the coated area adjacent to the edge. A change in density, for example, between 10% and 90% over a small distance indicates a sharp edge; the same change over a larger distance indicates a blurry edge. In some embodiments of the invention, the edge is characterized by a sharpness that corresponds to a change from 10% to 90% density over a distance of less than about 5 μm. In some embodiments, the distance is less than about 3 μm, less than about 2 μm, less than about 1 μm, less than about 0.5 μm, less than about 0.2 μm, or less than about 0.1 μm.

Without wishing to be bound by any particular theory, it is proposed that a certain degree of sharpness may be necessary in order to induce cell rolling along a particular direction. It is possible that at a sharp edge, cells can initiate an asymmetrical motion that is only possible when it interacts simultaneously with a surface coated with ligands that interact with the cell surface and with an uncoated surface.

Arrangement of Edge(s)

Figure 3:
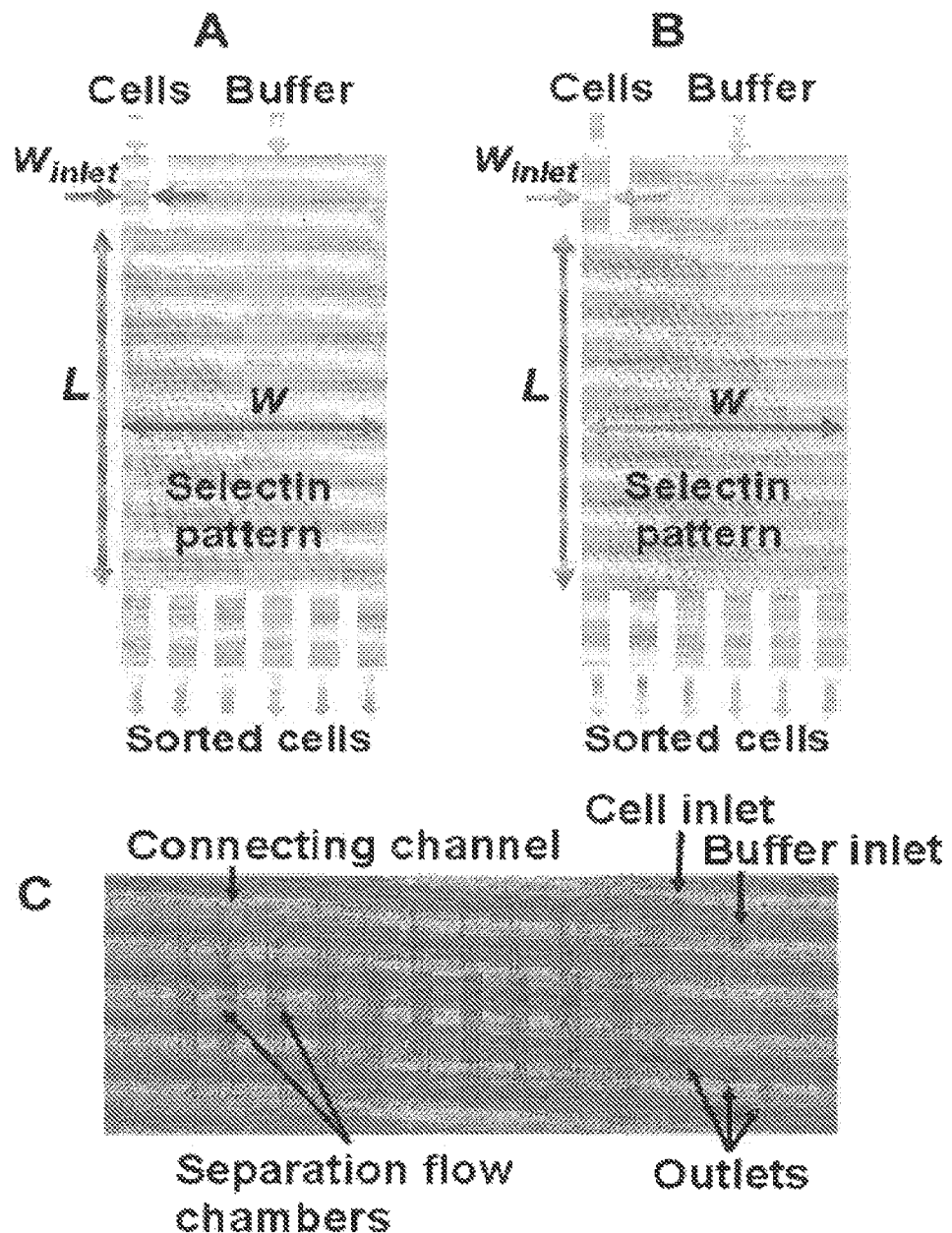
FIG. 3 illustrates that cell separation may be performed using flow chambers with selectin edges at varying angles (A) or a constant angle (B). Chamber length (L), width (w), cell inlet width ($w_{inlet}$), and chamber height (h) are design parameters that may be particularly relevant. As shown, in one embodiment, ten devices may be used in parallel for cell separation to increase throughput (C).
Figure 4:
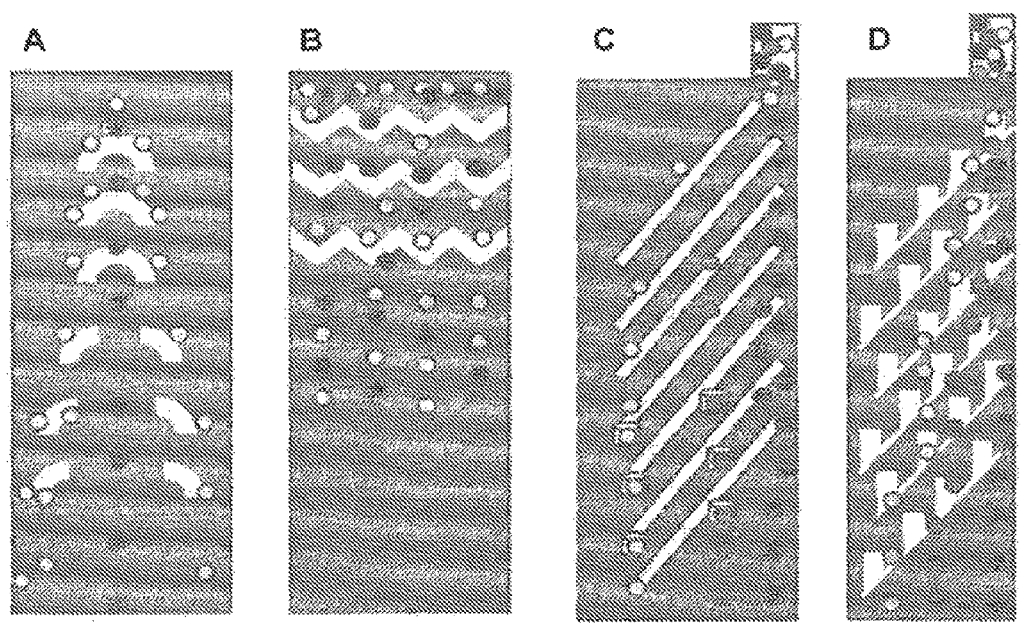
FIG. 4 depicts different design schemes that make use of the edge effect. (A) Negative selection of rolling cells away from cells that do not follow an edge. (B) Edges to arrange cells in single files. (C) Isolation of single cells by incorporation of microwells (which can also be adhesive patches to capture cells). (D) Adhesive areas leading to edges for enabling cells to roll before encountering the edge.

Areas coated with ordered layers may form any of a variety of designs that provide edges as discussed herein. Designs may comprise a plurality of coated areas. Some examples of designs are depicted in FIGS. 2-4.

In certain embodiments of the invention, designs comprise one or more coated areas that each define strips having at least two edges. The two edges of a strip may be substantially parallel; alternatively or additionally, the strips themselves may be substantially parallel to each other. In some embodiments wherein the strips are substantially parallel to each other, strips may be separated by a substantially fixed distance $w_g$ between adjacent strips and may have substantially the same width $w_s$. Both parameters $w_g$ and $w_s$ may be varied as appropriate, for example, to achieve cell-rolling based separation for a particular set of conditions. For example, $w_s$ may be in the range of from about 0.01 μm to about 10 mm. In some embodiments of the invention, $w_s$ is less than about 100 μm, less than about 75 μm, or less than about 50 μm. In some embodiments of the invention, $w_s$ is greater than about 0.1 μm or greater than about 1 μm.

It may be useful in some circumstances to define $w_s$ in relation to the average diameter d of a cell that may be induced to roll. In some embodiments, $w_s$ is less than 3d, less than 2d, or less than d.

$w_g$ may be, for example, in a range from about 0.2 μm to about 10 mm. In some embodiments, $w_g$ is less than about 100 μm, less than about 75 μm, or less than about 50 μm. In some embodiments, $w_g$ is greater than about 1 μm, greater than about 5 μm, or greater than about 10 μm.

$w_g$ may approximately equal, be greater than, or be less than $w_s$.

In certain embodiments, $w_g$, $w_s$, or both, may have a certain relationship with other parameters. For example, cells may roll along an edge with a contact radius $r_{contact}$. In some embodiments, $w_g > r_{contact}$. In some embodiments, $w_g$ is slightly bigger than $r_{contact}$, for example, $w_g$ may be bigger than $r_{contact}$ but limited such that $w_g < 1.5 \cdot r_{contact}$, $w_g < 1.2 \cdot r_{contact}$, or $w_g < 1.1 \cdot r_{contact}$.

Designs may comprise strips of coated areas that are not parallel to one another. In some embodiments, such strips originate from a common point, or from a common area such as an inlet, and radiate outward at different angles. One example of such a design is depicted in FIG. 3A.

Alternatively or additionally, designs may comprised coated areas defined by shapes such as, for example, squares, rectangles, triangles, polygons, ellipses, circles, arcs, waves, and/or combinations thereof. It will be appreciated that a plurality of such shapes and/or strips may be arranged into any design as long as the overall design provides at least one edge with a non-zero angle to the direction of flow across the surface. See, for example, FIGS. 2 and 4. In general, the nature of the design may be tailored depending on the type of cell(s) which is being separated and/or the type of separation which is desired. For example, when a system is needed to separate a single cell type then a simple design with a single type of edge may suffice. However, when a system is needed to separate a plurality of different cell types then a more complex design with different types of edges may be required.

Surfaces may incorporate additional elements or features for a particular purpose, e.g., capturing cells within the surface, as depicted in FIG. 4C. Elements may be physical structures, such as, for example, wells (i.e., depressions in the surface), that restrict cells from flowing in the direction of flow. Similarly, adhesive patches may be incorporated into surfaces to facilitate immobilization of cells in particular regions on the surface. Adhesive patches may comprise, for example, molecules such as antibodies that facilitate cells reducing their velocity and/or stopping. In certain embodiments, surfaces further comprise adhesive patches located adjacent to and/or leading to at least one edge. In some embodiments, adhesive patches are located upstream of a coated area. By "upstream" it is meant that the adhesive patches are located such that cells flowing over the surface encounter the adhesive patches before they encounter the coated area. Such adhesive patches may attract cells and facilitate cells rolling along the edges.

C. Cells

Populations of cells may comprise any of a variety of cell types and may be obtained from any of a variety of sources. Cell populations typically comprise at least one subpopulation of cells with a common characteristic.

In some embodiments of the invention, in the step of flowing, at least one cell in the subpopulation rolls at least part of the time. Such a cell may roll in a direction that is $\alpha_s$ to the direction of flow as a result of interaction with the edge, wherein $\alpha_s$ is the angle that forms between the edge and the direction of fluid flow. In some embodiments, substantially all cells in the subpopulation roll at least part of the time.

The common characteristic can be a phenotype such as expression of a cell surface moiety, cell type (such as, for example, lineage type), differentiation potential, etc. For example, cells in the subpopulation may all comprise a cell surface moiety that is recognized by the cell adhesion molecules. Examples of cell surface moieties include ligands of P-selectin, ligands of E-selectin, ligands of L-selectin, etc. Examples of such moieties include P-selectin ligand 1 (PSGL-1), CD44 (a ligand for E-selectin and L-selectin), glycosylation-dependent cell adhesion molecule 1 (GlyCAM-1, a ligand for L-selectin), CD15 (a ligand for P-selectin), CD34 (a ligand for L-selectin), E-selectin ligand 1 (ESL-1), etc. Further examples of surface moieties include Very Late Antigen 4 (VLA-4, a ligand for VCAM-1), gp200, etc.

Subpopulations may comprise particular cell types and/or combinations of cell types. For example, cells in a subpopulation may be cancer cells. Further examples of cell types include stem cells (e.g., mesenchymal stem cells, hematopoietic stem cells, embryonic stem cells, etc.), progenitor cells, red blood cells, neutrophils, lymphocytes, monocytes, white blood cells, etc. In some embodiments, all cells in a subpopulation are of a particular cell type, e.g., all cancer cells, all stem cells, all progenitor cells, etc. Though platelets are not formally classified cells, they may be induced to roll and separated using systems of the present invention.

Cells may be obtained from a variety of sources, including, but not limited to, bodily fluids containing cells (such as, for example, blood, lymph, ascites fluid, urine, saliva, synovial fluid, cerebrospinal fluid, vitreous humor, seminal fluid, etc), tissue samples, frozen stocks, cell cultures, etc.

Cells may be treated with agents before and/or as they are flowed. For example, cells may be treated with agents that modify their deformability. Examples of such agents include cytochalasin, N-ethylmaleimide, p-choloromercuribenzene, vinblastine, etc. In certain embodiments, this treatment step may facilitate cell rolling of a certain type of cell.

D. Cell Rolling

Figure 5:
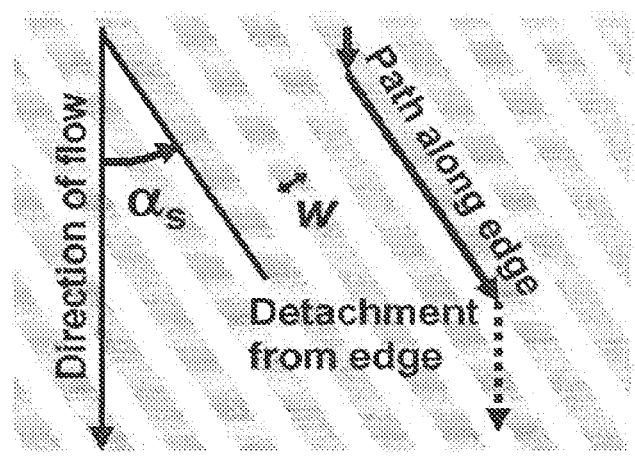
FIG. 5 is a schematic showing design parameters for selectin/mAb arrangements that comprise receptor bands of width (w) with edges making an angle ($\alpha_s$) with respect to the direction of flow. Also depicted is a possible path of a rolling cell that encounters the edge, follows it for a distance, and subsequently detaches from it.

Cells flowing close to the surface may, under appropriate conditions, roll across the surfaces of coated areas. Cells that are further away from edges (for example, more than one cell diameter away from the edge) generally will continue to roll in or approximately in the direction of fluid flow. In certain embodiments of the invention, cells at or near the edge (for example, within one cell diameter of the edge) roll along the edge at least part of the time. In some embodiments, cells that are away from the edge may roll in or approximately in the direction of fluid flow until they disengage from the surface or encounter an edge, at which point they may begin to roll along the edge. In some embodiments, cells rolling along an edge follow the edge for some time, disengage from the surface, reattach (for example, on another or on the same coated area), and begin rolling again. (See, for example, FIG. 5).

It will be appreciated that under a given set of conditions, not all cells in a population of cells may roll along the edge. Cell rolling may be selective in that only certain subpopulations of cells will roll. As an example, populations may comprise cells that do not comprise a cell surface moiety that is recognized by the cell adhesion molecules. Such cells would not roll along the surface under most conditions. Among cells in the population that do express a cell surface moiety recognized by the cell adhesion molecules, differences may exist that are permissible to rolling along the edge for one or more subpopulations, while not being permissible to rolling for other subpopulations. Without wishing to be bound by any particular theory, any of a number of characteristics may serve to differentiate the subpopulations that roll along an edge from those that do not under a given set of conditions. Such characteristics might include, for example, density of cell surface moieties, cell size, cell deformability, etc.

Direction

As mentioned above, cells may roll along edges, at least one of which forms a non-zero angle $\alpha_s$ with the direction of flow. Cells may, in some embodiments, therefore roll in a direction that is $\alpha_s$ from the direction of flow. As discussed above, $\alpha_s$ may vary. In certain embodiments, $\alpha_s$ is at least 0.5 degrees, $\alpha_s$ may be, in various embodiments, at least 1 degree, at least 2 degrees, at least 3 degrees, at least 4 degrees, at least 5 degrees, at least 6 degrees, at least 7 degrees, or at least 8 degrees. $\alpha_s$ may be, in various embodiments, less than about 70 degrees, less than about 65 degrees, less than about 60 degrees, less than about 55 degrees, less than about 50 degrees, less than about 45 degrees, less than about 40 degrees, less than about 35 degrees, less than about 30 degrees, less than about 25 degrees, less than about 20 degrees, or less than about 15 degrees.

Without wishing to be bound by any particular theory, cells may roll more easily at smaller angles and may tolerate angles up to a maximum angle $\alpha_{tr}$. $\alpha_{tr}$ may vary depending on characteristics of the cells, particular conditions of the cell separation system, etc.

Speed

Speed of cell rolling may also depend on characteristics of cells, on particular conditions of the system, etc. The speed of a cell rolling along an edge may, in some embodiments, be greater than the speed of a similar cell rolling on a coated area away from the edge. A given cell may roll with variable speed or with a substantially constant speed during the time it rolls along an edge. In some embodiments, cells within a subpopulation have uniform average speeds when rolling along edges of a given angle $\alpha_s$. In some embodiments, cells within a subpopulation have different average speeds when rolling along edges of a given angle $\alpha_s$.

Cells may roll along an edge, for example, in a direction that is $\alpha_s$ to the direction of flow at an average speed of at least about 0.1 µm/s, at least about 0.5 µm/s, at least about 0.8 µm/s, or at least about 1.0 µm/s.

Shear

Assuming a linear fluid velocity profile, shear on a cell may be related to fluid velocity in some embodiments as:

$$\tau = \mu \frac{V_{fluid}}{R_{cell}} \quad \text{(Eq. 1)}$$

wherein µ is the viscosity of the fluid, $R_{cell}$ is the radius of the cell, and $V_{fluid}$ is the velocity of fluid flow at distance Ra from the surface.

In some embodiments, the shear stress on cells flowed over the surface is in a range between about 0.05 dyn/cm² to about 50 dyn/cm². In some embodiments, the shear stress ranges between about 0.2 dyn/cm² to about 5 dyn/cm².

Cell Deformability

Without wishing to be bound by any particular theory, deformability of a given cell may influence its ability to roll along an edge. For example, in some embodiments, cells that are less deformable may be less amenable to rolling along an edge as are cells that are more deformable.

The area with which a cell contacts a surface as it rolls may give an indication of the deformability of the cell. For example, cells that interact with a surface with a large contact area may be more deformable than those that do so with a small contact area. Contact area may be defined, in some embodiments, by a contact radius $r_{contact}$.

In some embodiments, cells rolling along an edge contact the surface with a cell contact radius $r_{contact}$ of at least about 0.25 µm. In various embodiments, $r_{contact}$ may be at least about 1 µm, at least about 2 µm, at least about 3 µm, or at least about 4 µm.

Deformability of cells may be altered, for example, by treatment before and/or during flowing with an agent that modifies cell deformability, as discussed herein.

Relationships and Combinations of Parameters

In certain embodiments of the invention, parameters are defined in relation to each other.

In some embodiments, physical constraints guide relationships between two or more parameters. For example, $\alpha_s$ may in some embodiments and for certain designs be related to $w_s$ (width of strips of coated areas in certain designs) and/or $w_g$ (width of the gap between strips for certain designs). As another example, cell deformability may depend at least in part on cell size.

In some embodiments, two or more parameters are constrained intentionally by design. For example, as discussed herein, $w_g$ may be constrained to certain values based on $r_{contact}$ (cell contact radius). In some embodiments, $w_s$ may be fixed to equal $w_g$.

Relationships between parameters may be determined experimentally. For example, for each $w_s$ and/or $w_g$, the maximum angle $\alpha_{tr}$ at which cells can be made to roll on the edge with respect to direction of flow can be determined. The density of cell adhesion molecules may also affect $\alpha_{tr}$.

E. Cell Separation and/or Collection

In certain embodiments of the invention, methods further comprise separating at least one cell from certain cells in the population of cells. Methods may, in some embodiments, further comprise collecting one or more subpopulation of cells. Cell separation may facilitate diagnostic applications. For example, inventive methods may allow separation and, as a result, detection of certain types of cells such as activated neutrophils, circulating tumor cells, etc. Presence of such cell types in a biological sample may be indicative of certain conditions, diseases, etc. Separated and/or collected cells may in some embodiments be used in downstream applications, for example, to culture a subpopulation of cells that is present in low quantities in a starting population of cells or in a fluid. Separated and/or collected cells may have therapeutic value. For example, separated and/or collected stem cells may be used to regenerate tissue and/or function. Inventive methods may be particularly suitable for certain therapeutic applications, as cell rolling is a gentle process that does not interfere with cell physiology.

Separation may be based on different rolling characteristics of the at least one cell as compared to other cells from the population. For example, a subpopulation of cells sharing a common characteristic may be able to roll along an edge better (such as, for example, for a longer period of time before disengaging from the surface, with a greater speed, etc.) than other cells in the population. Cells in such a subpopulation, for example, may be directed along in a particular direction using an edge that is angled with respect to the direction of fluid flow, whereas cells that do not roll as easily are not diverted from the direction of flow.

In some embodiments, at least one cell of interest rolls along an edge and is diverted away from the direction of flow in a certain direction. The cell may be collected at one or more collection points along and/or at the end of the trajectory/trajectories of diverted cells.

In some embodiments, a "negative" selection scheme is used in which cells that do not roll along the edge are separated from others. For examples, edges may be designed to direct cells that roll along an edge away from a given collection point. Thus, cells that do not roll along the edge may be separated from others and/or collected. (See, for example, FIG. 4A and Example 14.)

Cell separation and/or collection may, in some embodiments, be facilitated by inventive devices disclosed herein.

F. Three-Dimensional Methods

In certain embodiments of the invention, methods are adapted for use in three dimensional systems. (See, for example, Example 15.) Such methods are similar to those already described, except that the edge effect is achieved using a "stagnation line" of no flow rather than or in addition to an edge. Generally, such methods comprise steps of providing a three dimensional surface that is at least partially coated with an ordered layer of cell adhesion molecules and flowing a population of cells across the surface. Fluid is flowed in such methods under such conditions as to create a stagnation line of no flow that forms an angle $\alpha_s$ with the direction of fluid flow. At least one cell in the population of cells being flowed comprises a cell surface moiety that is recognized by the cell adhesion molecules, and at least one cell in the population of cells rolls at least part of the time in a direction that is $\alpha_s$ to the direction of flow.

When flowing fluid encounters a certain kind of three dimensional object a "stagnation line" can be created. Any object and shape that creates differences in direction of flow can potentially be used to create a stagnation line. For example, cylinders, ridges, grooves, bumps, etc. may create a stagnation line. At least part of the outer and/or exposed surfaces of such objects and shapes may be coated with cell adhesion molecules that may induce cell rolling.

A cell rolling on the surface will roll towards the stagnation line, and then (under certain conditions) roll along the stagnation line and thereby follow it. Cells may roll in a direction at an angle to the direction of fluid flow when the stagnation line is at an angle to the direction of fluid flow. As in the case of rolling along an edge, cells may follow the stagnation line so long as the angle does not exceed a maximum angle $\alpha_{tr}$, whose value depends on the particular conditions of the cell separation system. The stagnation line may be curved depending on the surface under consideration and the flow field around the surface. Therefore, the stagnation line can act as an edge and facilitate cell rolling.

Figure 6:
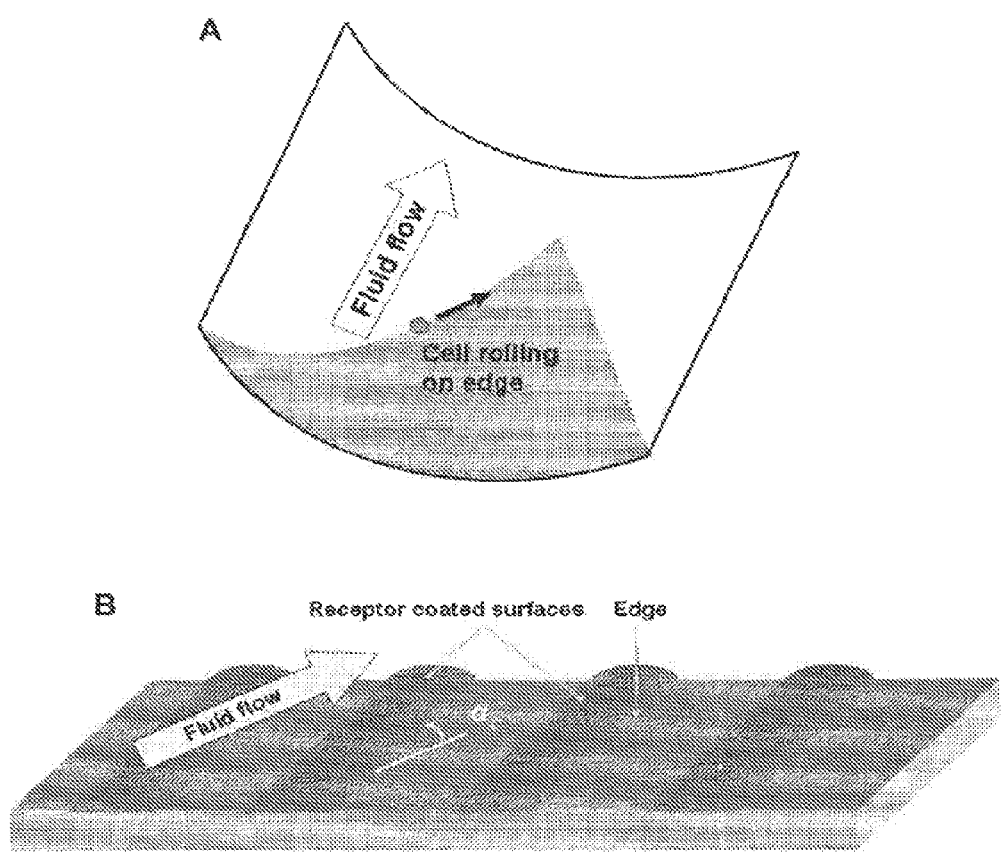
FIGS. 6A and 6B depict three dimensional surfaces which comprise edges on which cells can be made to roll. Such surfaces may or may not create stagnation lines; nevertheless, they may influence the direction of cell rolling through the edges.

In certain embodiments, three dimensional surfaces comprise at least one edge as discussed herein and may or may not include a stagnation line, as depicted in FIGS. 6A and B. For example, the edge may be on a spherical, cylindrical, etc. surface. Edges may also be along a wavy surface, along a surface with periodic bumps, etc.

II. Devices

In some aspects of the invention, devices for cell separation are provided. In certain embodiments, such devices are designed to be used in accordance with methods of the invention. Generally, such devices comprise a separation flow chamber, an inlet for flowing cells into the separation flow chamber, and an outlet for flowing cells out of the separation flow chamber, wherein the separation flow chamber comprises a surface that is at least partially coated with an ordered layer of cell adhesion molecules, and wherein the surface comprises at least one edge between an area coated with the ordered layer and another area that is not coated with the ordered layer. In such devices, when cells are flowed through the inlet to the outlet, they flow at an angle $\alpha_s$ to the direction of the at least one edge unless they interact with the at least one edge.

Devices of the invention may comprise any of the features disclosed above in the discussion of inventive methods.

It is to be understood that a device may include any number of inlets or outlets as may be required for a particular application. For example, in certain embodiments, a device may further comprise an additional inlet for introducing a buffer stream free of cells into the separation flow chamber. A plurality of outlets may be useful, e.g., when it is desirable to collect cells which are differentially separated as a result of flowing through the separation flow chamber.

The separation flow chamber may have any shape, e.g., without limitation, a square or rectangular shape.

Without wishing to be bound by any particular theory, the height of the separation flow chamber may influence the percentage of cells being flowed that is forced to interact with the surface. It may be desirable, in some embodiments, to limit the height such that more cells flowing through the separation flow chamber interact with the surface. In some embodiments of the invention, the walls defining the separation flow chamber have a height ranging from about 5 μm to about 1 mm. In various embodiments, the height of such walls is less than about 100 μm, less than about 75 μm, less than about 50 μm, less than about 25 μm, or less than about 15 μm. The height may not be uniform through the length of the separation chamber. For example, the height may vary across the length of the separation chamber in steps.

In certain embodiments, the separation flow chamber may be defined by a lower partially coated surface, walls and an upper uncoated surface. In certain embodiments, a single device may include a plurality of separation flow chambers each with their own inlet(s) and outlet(s).

In certain embodiments, these separation flow chambers may be separate and unable to communicate (i.e., a parallel system). Each separation flow chamber in such a device may be include the same or a different edge design. Devices which include a plurality of separation flow chambers with the same edge design may be useful when there is a need to replicate a separation under similar conditions (e.g., one or more test samples and a control sample). Devices which include a plurality of separating flow chambers with a different design may be useful when there is a need to identify a design which produces optimal separation (e.g., using different aliquots of the same test sample).

In certain embodiments, a device may include two or more separation chambers that are in fluid communication (e.g., where the outlet from a first separation chamber feeds into the inlet of a second separation chamber). Each separation flow chamber in such a device may be include the same or a different edge design. It will be appreciated that such serial set ups may be useful when, for example, it is desirable to expose a subpopulation of cells which has been isolated by a first separation phase to a second separation phase (e.g., to isolate sub-subpopulations).

It will be appreciated that any combination or permutation of the aforementioned embodiments is encompassed by the present invention.

In certain embodiments of the invention, inventive devices may be used in conjunction with other devices. For example, cells flowing out of the outlet of one device may flow into another device. Alternatively or additionally, devices may be fabricated such that they receive (into their inlets) cells flowing from another device.

In certain embodiments, devices further comprise one or more means for collecting at least a subpopulation of cells flowed through the separation flow chamber (e.g., one or more channels at one end of the separation flow chamber). It will be appreciated that any of the aforementions methods may comprise steps which make use of such means for collecting cells. In some embodiments, a porous filter may be situated at one end of the channel. A plurality of channels may be used in devices for collection of supopulations of cells. In some such embodiments, devices further each comprise a plurality of porous filters that may be situated, for example, at the ends of collection channels and/or between sequential channels.

Figure 7:
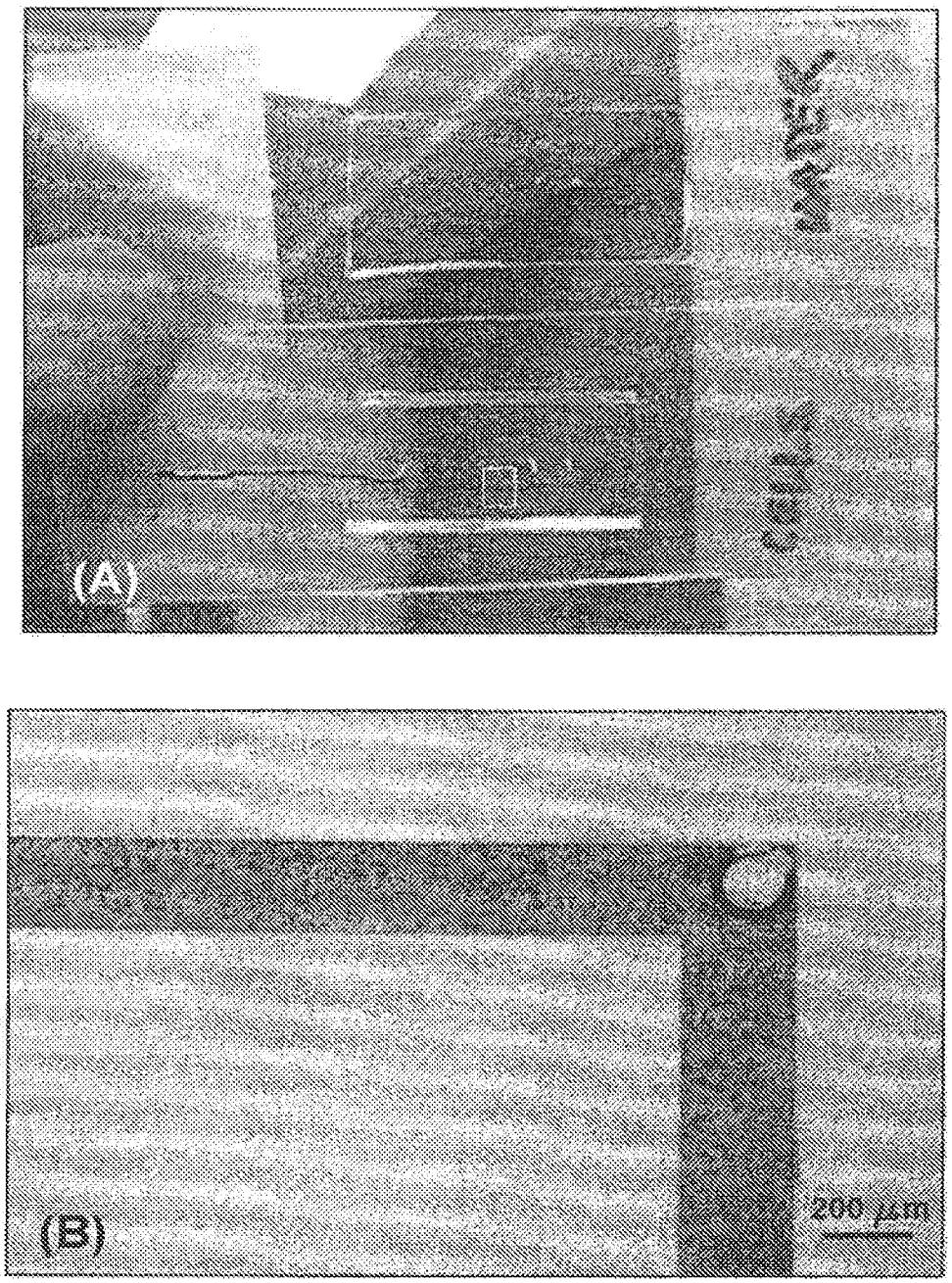
FIG. 7: (A) a microchannel (of a PDMS device bonded on a glass slide) filled with water may be difficult to see by eye due to lack of scattered light (top slide). A similar microchannel filled with cells is easily visualized and distinguished by light scattered by the cells (bottom slide). (B) Magnified view of the inset (marked by a square in (A)) showing cells trapped in the microchannel.

Devices may be designed and/or built such that it is possible to visualize collected cells easily. For example, collected cells may be visualized by eye, using a low power microscope, using a magnifying lens, or combinations thereof (e.g., see FIG. 7, which shows a channel that can be visualized by eye when the channel is filled with cells). In some embodiments, visualization of collected cells in the channel is facilitated by illumination with light. Device elements that aid visualization of cells may in some embodiments be incorporated into the device. For example, a magnifying lens may be built into the device and situated such that it magnifies the collection channel. Alternatively or additionally, collected cells may be visualized with the help of colored fluid, dyes, etc, or combinations thereof. In some embodiments, estimates of the numbers of collected cells can be obtained without further processing. In some such embodiments, devices may incorporate, for example tick marks along the collection channel such that the height of the column of collected cells gives an indication of the cell volume and/or of the cell count.

In certain embodiments, devices further comprise a means for controlling flow rate. In some embodiments, the means for controlling flow rate is a syringe pump.

In general it is to be understood that while liquid fluid flow has been used in may of the embodiments described herein, flow of cells in an inventive method or device may be accomplished by a variety of means. Thus, while cells may be flowed in a fluid, cells may also be flowed using capillary action. Thus, in some embodiments, cells are flowed in a vacuum. In some embodiments, cells are flowed at least in part due to a force or forces such as, for example, gravitational forces, electrokinetic forces, centrifugal forces, and combinations thereof.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

P-Selectin-Coated Surfaces

It may be desirable in certain applications such as those described herein to be able to control the presentation of biomolecules on surfaces. For example, controlling the density and conformation of biomolecules on surfaces and enhancing stability of such coated surfaces could allow tuning of such surfaces for particular applications. Also, co-immobilization of secondary molecules may facilitate selective separation of certain types of subpopulations such as mesenchymal stem/progenitor cells.

Covalent immobilization of biologically active species may be advantageous for controlling parameters such as density, conformation, and enhanced stability. Although covalent immobilization procedures for peptides and enzymes have been studied for decades, covalent immobilization of large molecular weight biomolecules such as selectins present significant challenges. Among such challenges are increased binding to non-specific sites and a requirement for mild processing conditions to prevent protein inactivation.

In the present Example, P-selectin was covalently immobilized onto glass substrates and characteristics (such as, for example, orientation, density, and stability of P-selectin molecules, etc.) of such coated surfaces were examined.

Materials and Methods

Recombinant Human P-selectin/Fc chimera (P-selectin) and Human Fc antibody fragments were purchased from R&D Systems (Minneapolis, Minn.). SuperClean unmodified glass slides and SuperEpoxy® (ArrayIt®) functionalized slides were obtained from TeleChem International Inc. (Sunnyvale, Calif.). Heterobifunctional poly(ethylene glycol) ($NH_2$-PEG-COOH) was acquired from Nektar Therapeutics (San Carlos, Calif.). SuperAvidin™-coated microspheres with a diameter of 9.95 μm were obtained from Bangs Laboratories. Multivalent biotinylated Sialyl Lewis (x)-poly(acrylamide) (sLex-PAA-biotin) and a rectangular parallel-plate flow chamber with a 250 μm thick gasket were obtained from Glycotech. All other chemicals used in the present Example were obtained from Signa-Aldrich (St. Louis, Mo.).

Materials employed in the present Example were used without further purification unless specified.

Preparation of Surfaces

Figure 8:
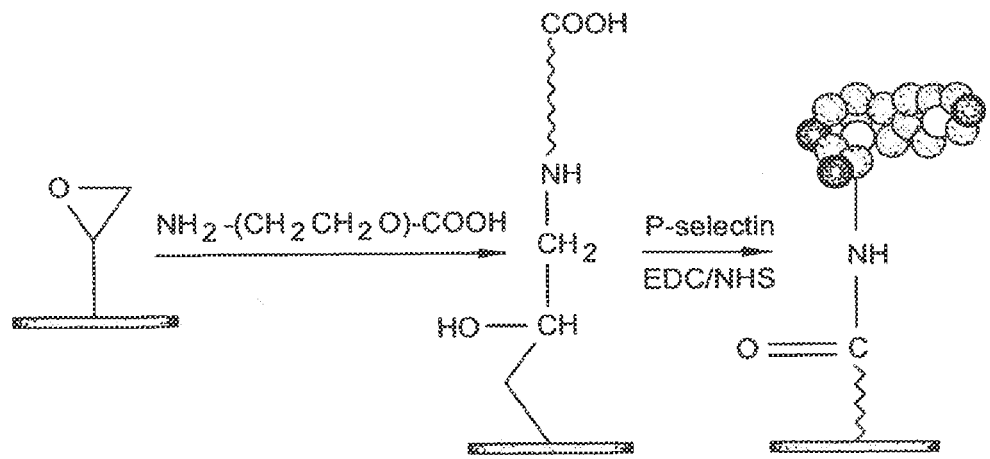
FIG. 8 depicts a reaction scheme of covalent immobilization of P-selectin on an epoxy functionalized glass substrate. P-selectin is immobilized on top of a layer of polyethylene glycol pre-immobilized on the surface.
Figure 9:
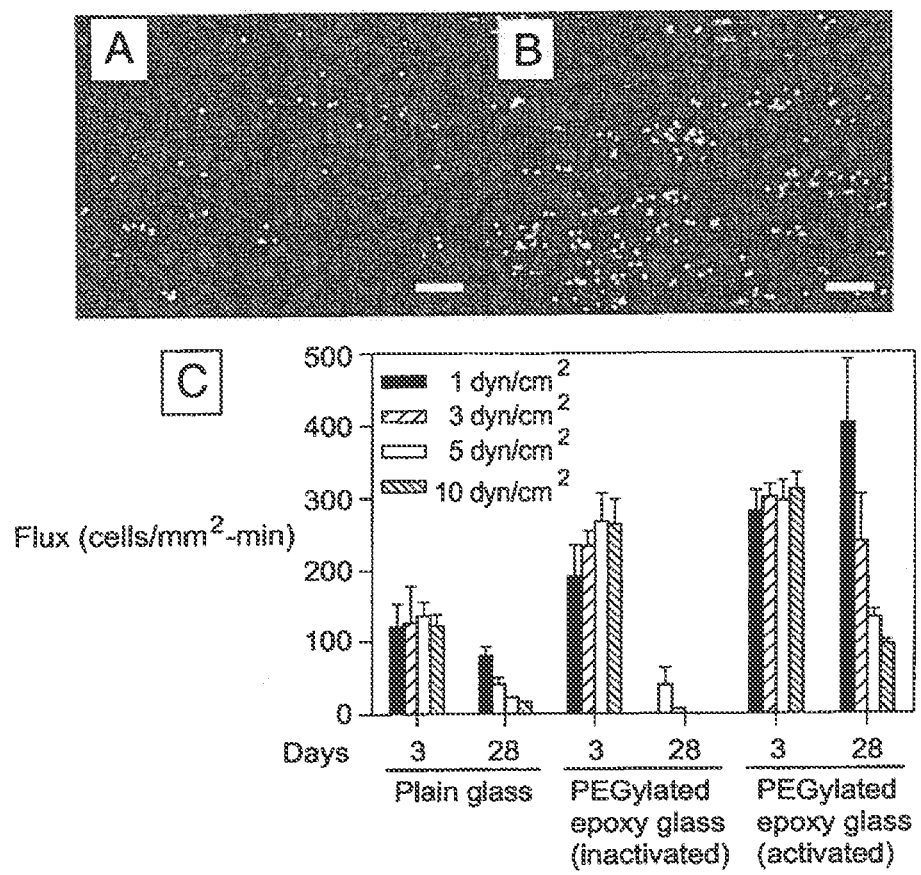
FIG. 9 shows still images and date on cell rolling on covalently immobilized vs. physisorbed P-selectin. A comparison of number of cells rolling on the surfaces after 28 days is shown in (A) physisorbed versus (B) covalently immobilized P-selectin. In (C), rolling dynamics of neutrophils on P-selectin-coated surfaces under shear flow are shown. $2.5 \times 10^5$/mL of neutrophil solution was perfused on a 3 or 28-day-old P-selectin-surface under wall shear stresses from 1 to 10 dyn/cm². Cells were counted as rolling cells if their velocity was below 50% of free flow velocity. Note that a significantly larger number of cells roll on the surface with covalently immobilized P-selectin as compared to the surface with physisorbed P-selectin.

As illustrated in FIG. 8, glass substrates containing epoxy groups (SuperEpoxy®) were first coated with 5 mg/mL of bifunctional poly(ethylene glycol) ($M_n$ 5,000) as a spacer to provide reactive sites (carboxylic ends) to P-selectin and non-fouling surfaces. Carboxylic acid groups on the PEG linker were pro-activated using EDC and NHS, followed by reaction with P-selectin solution (5 μg/mL) at room temperature overnight. Resulting surfaces were washed with PBS thoroughly and stored at 4° C. for later use. P-selectin physisorbed surfaces were also prepared on plain glass and on PEGylated glass without EDC/NHS activation to be used for comparison. Each step of the immobilization process was confirmed by contact angle measurement and X-ray photoelectron spectroscopy (XPS) (Data not shown).

Results and Discussion

P-selectin-coated surfaces were prepared on epoxy-coated slides and analyzed as discussed below.

Enhanced Functional Stability as Determined by Rolling of Microspheres and Live Cells Avidin-coated microspheres were conjugated with multivalent biotinylated Sialyl Lewis(x)-poly(acrylamide) (sLex-PAA-biotin) and used as a cell mimic. For flow experiments using the microsphere conjugates, a rectangular parallel-plate flow chamber with a 250 μm thick gasket was placed on the glass surfaces with P-selectin. Multivalent sLex-coated microspheres (approximately $5 \times 10^5$/mL) were perfused into the flow chamber at a shear stress of approximately 0.24 dyn/cm². Images were taken every 5 seconds and velocities (averaged over at least 20 microspheres) were calculated by measuring the displacement of each microsphere in consecutive images.

Freshly prepared surfaces exhibited significantly lower microsphere velocities compared to unmodified surfaces. Microsphere conjugates traveled on PEGylated surfaces without P-selectin at average velocities of 30-40 μm/s, which was in reasonable agreement of 57 μm/s according to Goldman's calculation (Goldman et al. 1967. "Slow viscous motion of a sphere parallel to a plane wall. II Couette flow." *Chemical Engineering Science.* 22: 653-660, the entire contents of which are hereby incorporated by reference in their entirety).

After 21 days in PBS at room temperature, P-selectin covalently immobilized onto epoxy glass exhibited a significantly better long term stability compared to both physisorbed P-selectin and unactivated surfaces (without NHS/EDC). P-selectin immobilized surfaces (pre-activated) exhibited the highest reduction in the microsphere velocity, with microspheres traveling at ~40% of their velocities on PEGylated epoxy surfaces without P-selectin. P-selectin immobilized on epoxy glass untreated with EDC/NHS and P-selectin-adsorbed plain glass allowed microsphere conjugates to travel relatively faster. On P-selectin immobilized epoxy glass untreated with EDC/NHS and the P-selectin-adsorbed plain glass, sLex-PAA-conjugated microspheres traveled at ~85% and ~70% respectively of their velocities on surfaces on PEGylated epoxy surfaces without P-selectin.

Neutrophil rolling interaction with the immobilized P-selectin was also investigated using a parallel-plate chamber under flow. A suspension of $2.5 \times 10^5$/mL neutrophils was perfused into the chamber at different flow rates corresponding to wall shear stresses ranging from 1 to 10 dyn/cm$^2$. A cell was classified as rolling if it rolled for >10 seconds while remaining in the field of view ($864 \times 648$ μm$^2$ using a 10× objective) and if it translated at an average velocity less than 50% of the calculated free stream velocity of a non-interacting cell. Control surfaces that did not have P-selectin (i.e., plain glass and a PEGylated epoxy glass slides) showed no cell adhesion (data not shown).

Figure 10:
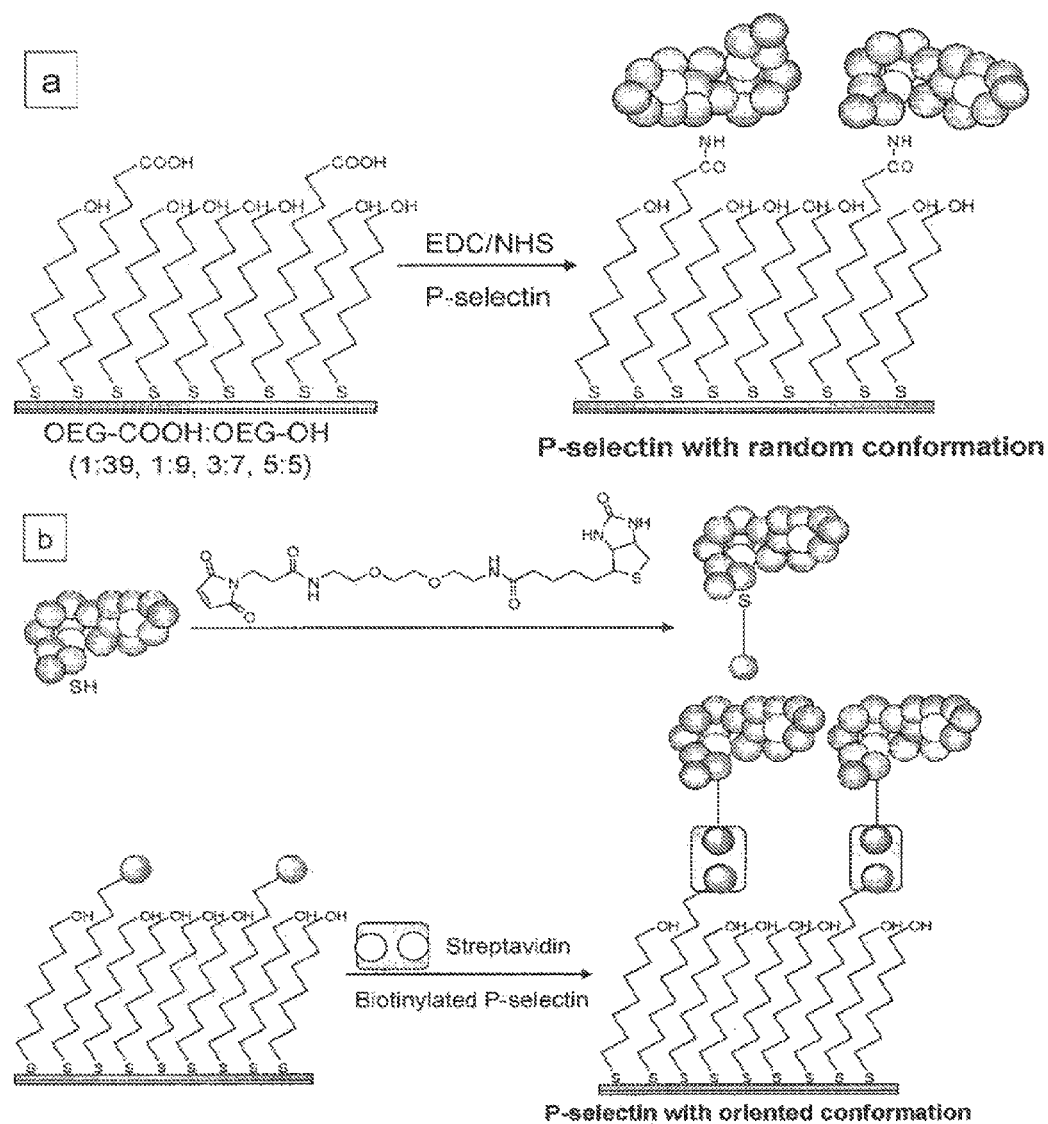
FIG. 10 depicts schematic diagrams of P-selectin immobilization on (A) mixed self-assembled monolayers (SAMs) of OEG-COOH/OEG-OH at different ratios using the EDC/NHS chemistry and (B) mixed SAMs of OEG-biotin/OEG-OH after biotinylation of P-selectin through conjugation through —SH group of P-selectin. Note that P-selectin immobilized through amide bonds (A) and through biotin-streptavidin bonds (B) should have random and oriented conformation on the surfaces, respectively.

The stability of covalently immobilized P-selectin is evident from this in vitro cell rolling assay at four different wall shear stresses (1, 3, 5 and 10 dyn/cm$^2$). The number of rolling cells significantly decreased with time for surfaces prepared by physisorption of P-selectin, but remained unaffected for covalently immobilized P-selectin even 28 days after preparation (FIGS. 10A and 10B). Specifically, at 3 dyn/cm$^2$, rolling flux on aged surfaces with covalently immobilized P-selectin did not exhibit a significant decrease (80.6±19.1% (mean±SEM), but fluxes on aged P-selectin adsorbed surfaces dropped to 30.1±5.2%, respectively.

Real Time Analysis of Covalent Immobilization Using SPR

To quantitatively characterize immobilization chemistries and their effects on ligand binding, surface plasmon resonance (SPR) was employed. This flow-based SPR system offers: 1) easy surface functionalization using thiol chemistries due to the presence of a gold layer and 2) quantitative and real time monitoring of binding events without any modification of analytes. Therefore, the SPR technique is useful particularly for determining controllability of density and orientation of P-selectin.

We developed chemistries to achieve non-fouling surfaces property and to provide reactive sites for subsequent P-selectin immobilization using oligo(ethylene glycol)-alkanethiols (Prochimia, Poland) on gold coated SPR chips. Immobilization on non-fouling PEG surfaces is advantageous because: 1) it reduces non-specific interaction due to a high content of PEG-OH groups, 2) it facilitates controllability of density/orientation by changing ratios between bi- and mono-functional PEG components, which is easier and more reproducible than using different P-selectin concentrations, and 3) it potentially enables introduction of multiple chemistries on the same surface.

Self-assembled monolayers (SAMs) were formed by soaking clean gold coated substrates in a 100 μM solution of OEG-alkanethiols in ethanol at room temperature overnight. The following mixtures of different OEG-alkanethiols were used at the indicated molar ratios: OEG-COOH:OEG-OH (1:39, 1:9, 3:7, 5:5) and OEG-biotin:OEG-OH (1:9). SAMs were rinsed, dried and degassed before introduction into the SPR instrument.

P-selectin was immobilized onto the surfaces of mixed SAMs of OEG-COOH/OEG-OH as shown in FIG. 10A. 10 mM phosphate buffer (PB) was first flowed into a chip at a flow rate of 50 UL/min for 5 min. A 1:1 (v/v) mixture of excess EDC and NHS was injected to activate carboxyl groups on the SAMs for 10 min. After flowing for 5 min, P-selectin at a concentration of 20 μg/mL in PB was injected and flowed for 7 min for immobilization. The chip surface was then washed with PB for 5 min, followed by ethanolamine (100 mM in PB) to deactivate remaining active ester groups and to remove loosely bound P-selectin from the surface.

For P-selectin immobilization on a mixed SAM of OEG-biotin/OEG-OH, P-selectin was first biotinylated using maleimide-PEO$_2$-biotin (Pierce) before SPR measurement as shown in FIG. 10B. A solution of P-selectin at 50 μL of 1 mg/mL P-selectin in PBS was mixed with 50 molar excess maleimide-PEG$_2$-biotin solution at 4° C. overnight. The reaction mixture was purified by 4 cycles of ultrafiltration using a 10K molecular weight cut-off membrane. Each cycle was performed at 14,000×g for 30 minutes. The mixed SAM of OEG-biotin/OEG-OH was mounted on the SPR and 10 μg/mL streptavidin in PBS was flowed for 10 minutes to create binding sites for biotinylated P-selectin. P-selectin was then immobilized under the same condition used for other mixed SAM surfaces via strong biotin/avidin binding. Immobilization in the SPR was carried out at a flow rate of 50 μL/minute.

Stable and Tunable P-Selectin Immobilized Surfaces Characterized by SPR

Figure 11:
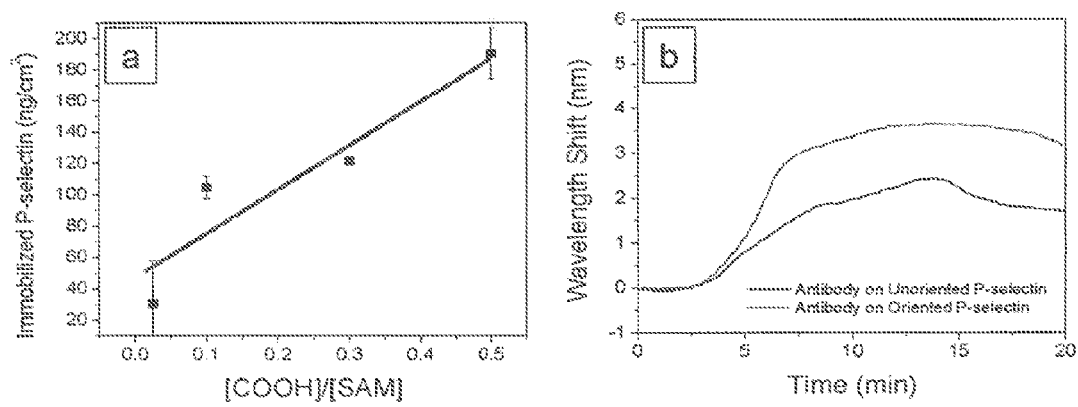
FIG. 11 shows (A) Surface plasmon resonance (SPR) sensorgrams of P-selectin immobilization with density controlled. By changing the ratio between OEG-COOH and OEG-OH, the amount of P-selectin immobilized is controlled and is proportional to the concentration of OEG-COOH. (B) Effect of P-selectin orientation on antibody binding by comparison of antibody binding on the unoriented P-selectin (EDC/NHS chemistry) and oriented P-selectin (thiol specific biotin-streptavidin chemistry). Note that the amounts of immobilized P-selectin were comparable for each other (~12 nm wavelength shift (~180 ng/cm²) for both surfaces).

To compare covalent immobilization with physisorption, some SPR channels were used as reference channels where P-selectin was adsorbed on the surface without EDC/NHS activation. Covalently immobilized P-selectin appeared to be stable, whereas physisorbed P-selectin was readily detached from the surface when washed with 150 mM Tris-HCl buffered saline (FIG. 11). To control density of P-selectin, mixed SAMs of OEG-COOH/OEG-OH at different ratios (using the chemistry shown in FIG. 10A) were used and P-selectin was immobilized under the same condition described above. FIG. 11A shows that the amount of P-selectin was linearly proportional to the amount of —COOH containing SAM component. Immobilization density could thus be controlled using mixed SAMs.

Orientation effect of P-selectin was also examined by comparing the two different chemistries in FIG. 10A (random conformation) and FIG. 10B (oriented conformation). Because a P-selectin molecule has many amine groups that can react with —COOH groups on the surface, conformation of P-selectin ought to be random. In contrast, P-selectin is known to possess only one cysteine as its 766th amino acid (P-selectin used in this study is composed of 1-771 amino acids of its natural form) on the other side of active binding sites at N terminal. For channels prepared using both chemistries, comparable amounts of P-selectin were first immobilized (~12 nm in wavelength shift), followed by flowing 20 μg/mL P-selectin antibody (eBioscience) at a flow rate of 20 μL/min. Channels with oriented P-selectin exhibited a significantly greater binding response than that from the channels with randomly immobilized P-selectin (FIG. 11B), indicating that orientation of P-selectin was controlled by using thioether chemistry.

In this preliminary study on covalent immobilization, we have shown that P-selectin can be covalently immobilized on surfaces, which provides better stability (as compared to physisorption) and control of density as well as orientation of P-selectin. These results suggest that stable and tunable surfaces can be prepared using the developed chemistries. Stable and tunable surfaces may be especially advantageous for consistency and for effective separation of cell subpopulations.

Example 2

Creation of P-Selectin Edges on Substrates

As described herein, coated surfaces with edges can facilitate cell rolling based separation. In the present Example, edges between P-selectin-coated areas and uncoated areas were created on glass substrates using silicone rubber masks.

Materials and Methods

Human P-selectin/Fc chimera (R&D Systems) was deposited on clean glass slides (SuperClean2, Telechem Inc.) using silicone gaskets as blocks to prevent parts of the glass substrate from P-selectin adsorption during physisorption of P-selectin. Clean silicone pieces were placed on the glass slide with their edges aligned at the desired angle to the edge of the glass slide. Glass slides were rinsed twice with 1×PBS, and 5 µg/mL P-selectin (in 1×PBS) was adsorbed overnight on exposed areas of the slides. Slides were then rinsed with 1×PBS, silicone pieces were removed, and the entire surface was blocked with 5% FBS or BSA. For some slides, BSA-FITC (Sigma-Aldrich) was used instead of BSA or FBS for blocking in order to visualize the P-selectin coated areas.

Results and Discussion

Figure 12:
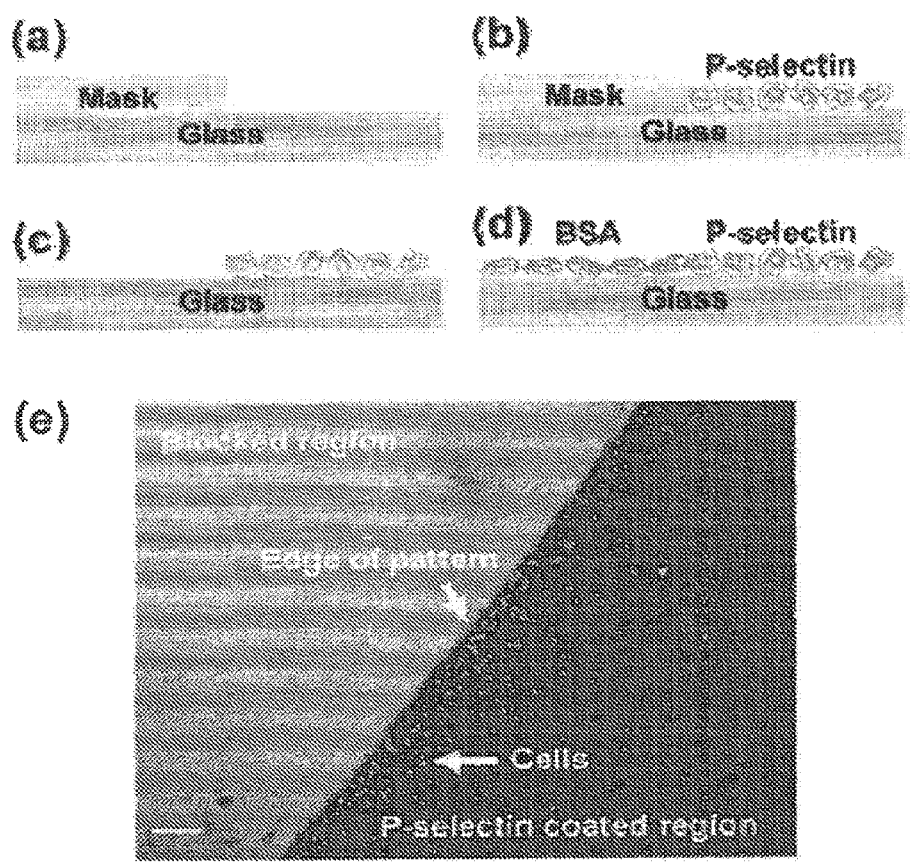
FIG. 12 depicts a schematic and an image illustrating immobilization of P-selectin to create edges. A silicone rubber mask was placed on a glass substrate (A), and P-selectin was coated on the exposed area of the substrate by physisorption (B). The silicone mask was then removed from the substrate (C), and BSA was used to block the areas that were not coated with P-selectin (D). Use of fluorescein-labeled BSA enabled visualization of the P-selectin arrangement using an epifluorescence microscope (E). HL-60 cells adhered selectively to the P-selectin region, confirming coating of some areas of the substrate with P-selectin. Scale bar: 100 μm
Figure 13:
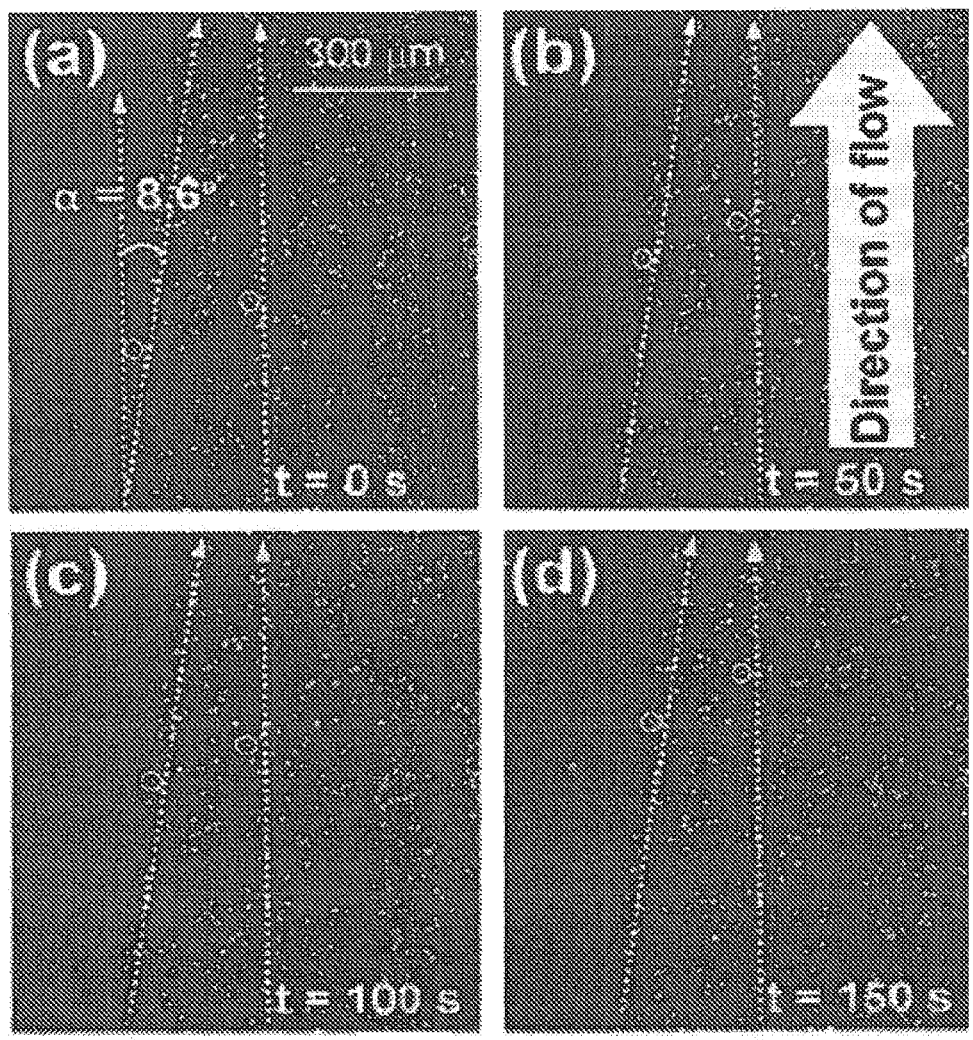
FIG. 13 shows photographs illustrating that a P-selectin edge directs motion of rolling cells. Rolling HL-60 cells that encountered the edge of a P-selectin-coated area making an angle to the fluid flow direction were forced to roll along the edge. The motion of a cell forced to roll along the edge is compared with another cell rolling in the direction of fluid flow, highlighted by circles. The edge succeeded in changing the direction of motion of the rolling cell by 8.6°, resulting in effectively displacing the cell by 0.15 mm from its original position for every 1 mm of length along the direction of flow. Wall shear stress was 1.9 dyn/cm².

Although covalent immobilization of P-selectin enhances surface properties such as functional stability, proof-of-concept studies do not require long-term stability and physisorption of P-selectin on glass substrates is sufficient. Selective physisorption of P-selectin was achieved using a silicone rubber mask in order to deposit P-selectin on glass substrates (FIG. 12). Use of bovine serum albumin conjugated with fluorescein isothiocyanate (BSA-FITC) during the blocking step revealed selective adsorption of BSA in the region occupied by the silicone mask as compared to the P-selectin coated region. Coated areas had well-defined edges, showing that the silicone mask did not leak during the physisorption step. Furthermore, when cells were flowed over this substrate, the cells selectively interacted with the region coated with P-selectin, confirming the success of the technique (FIGS. 1A, 1B, and 13E).

Example 3

Directing Cell Rolling on a Substrate Comprising an Angled Edge

In this Example, the direction of cell rolling was influenced using a substrate comprising P-selectin molecules forming a coated surface with an edge angled to the direction of fluid flow, demonstrating the potential feasibility of separating cells using cell rolling along an angled edge.

Materials and Methods

P-selectin coated surfaces were generated as described in Example 2, with an edge between a coated region and an uncoated region. Edges were angled at a various directions with respect to the direction of flow.

Cell and Microsphere Rolling Experiments in a Flow Chamber

Cell and microsphere rolling experiments were performed in a commercially available rectangular parallel-plate flow chamber 1 cm wide, 6 cm long, and 125 µm deep (250 µm for microspheres) (Glycotech Inc.). HL-60 cells at densities of $3-5 \times 10^5$/mL in cell culture medium or microspheres at densities of $10^5$/mL in 1×PBS buffer with 1% BSA were loaded in 5 mL syringes mounted on a syringe pump (New Era Pump Systems, Inc., Farmingdale, N.Y.) for controlling the flow rate. Flow rates were varied between 50 and 2000 µL/min, with corresponding shear stresses of 0.32-12.8 dynes/cm2 (0.032 to 1.28 Pa). When cells were flowed, human Fc fragments at 5 µg/mL were added to the cell suspension before the experiments in order to minimize interactions of the HL-60 cells with the Fc part of the P-selectin chimera. The flow chamber was mounted on an Axiovert 200 Zeiss microscope (Carl Zeiss, Thonwood, N.Y.) and images were obtained using a 10× objective typically at a rate of 1 frame per second for cell rolling and 3 frames per second for microsphere rolling for duration of 1 to 4 minutes. Flow was laminar (Re ~0.1-3) and shear stress (τ) was calculated using plane Poiseuille flow using the equation $$\tau = \frac{6\mu Q}{wh^2} \quad \text{(Eq. 2)}$$

where µ is the kinematic viscosity, Q is volumetric flow rate, w is width of the flow chamber, and h is height of the flow chamber.

Data Analysis

To facilitate data analysis, images were adjusted to the same extent for brightness, contrast, and gamma correction and processed using a home-made Matlab particle tracking software built around a particle tracking freeware. Images were filtered using a spatial filter and brightness threshold in order to identify cells. This step was verified by comparing Matlab-generated plots of cell positions with the real image in order to ensure that there were no spurious effects during image processing. Cell position was further located with sub-pixel resolution by averaging over the pixel intensities to locate the centroid of the pixels. These data for the entire set of images were consolidated into particle tracks listing the positions of rolling cells at each point in time. Tracks with the cell missing in even one image were discarded, as were tracks corresponding to stuck cells in which the cell did not show significant displacement (30 µm over the entire sequence of images). The particle tracking program was set to a threshold of a maximum displacement of 15 µm per frame; thus free-flowing cells were not tracked. The final result was a list of positions of each cell at each point of time, which could be used for visualization and further analysis. Average cell velocities were obtained by dividing the displacement between the start and end positions of the track by the elapsed time. The edge of the P-selectin coated region was easily identified from the particle tracks as tracks were present only in the P-selectin coated region, and could be represented by a line. In order to elucidate the effect of the edge on cell rolling, tracks that started within 15 µm of the edge were analyzed for velocity and compared with tracks that started beyond 90 µm of the edge. Average velocities and velocity distributions were obtained for each set of tracks. Microsphere data were also similarly analyzed.

Results and Discussion

We investigated the effect of a single edge of P-selectin on the motion of rolling HL-60 cells, a human myeloid cell line that expresses high levels of P-selectin glycoprotein ligand-1 (PSGL-1) that mediates cell rolling on selectins. Rolling behavior of HL-60 cells has been characterized in a number of studies, including dependence on shear rate, cell rigidity and topology, and capture in a microfluidic device. HL-60 cells are robust and easy to maintain and also express levels of PSGL-1 that are comparable to leukocytes, making them suitable candidates for proof-of-concept studies.

Suspensions of HL-60 cells at densities of 3-5×10$^5$ cells/mL were flowed over the substrates generated in Example 2 at a shear stress of about 0.32 to about 12.8 dyn/cm$^2$ (0.03-1.28 Pa) using a commercially available flow chamber. The flow chamber was rectangular with a width of 1 cm, height of either 125 µm (for cells) or 250 µm (for microspheres), and length of 6 cm, with inlet and outlet at either end.

Only some of the cells interacted with the surface, and the remaining cells flowed through the chamber without interacting with the surface. Only those cells that interacted with the surface were analyzed. Selective rolling of HL-60 cells was observed on the P-selectin coated region with slower cell rolling velocities than those on the BSA-coated region where cells were not hindered by the formation of adhesive bonds. Typical velocities of the rolling cells in our experiments ranged from about 0.3 to about 1.2 µm/s for shear stresses ranging from about 0.32 to about 12.8 dyn/cm$^2$, which are either comparable to or smaller than cell rolling velocities reported in other studies.

Remarkably, when rolling HL-60 cells encountered the edge of the P-selectin region, they were diverted from their original direction of travel along the direction of the edge, demonstrating that an edge could indeed be used to control the transport of cells through transient receptor-ligand adhesive bonds. Under the conditions of this particular experiment, this effect was observed only for small angles (<ca. 10-15°) between the edge and the direction of flow, and nearly all cells that encountered the edge were deflected from their original direction of travel and forced to follow the P-selectin edge. No edge effect was observed at larger edge angles; cells that encountered the edge detached from the substrate and continued to flow in the direction of fluid flow. Thus, in the conditions of this particular experiment, the direction of travel of the cells could be changed only at smaller edge angles. FIG. 12 shows snapshots of cells rolling under a shear stress of 1.9 dyn/cm$^2$ (300 µL/min) with two cells highlighted, one cell in the P-selectin coated region that did not encounter the edge and another cell that encountered the edge and was forced to travel along the edge. The cell that encountered the edge was deflected from its direction of fluid flow and traveled at an angle of 8.6° with respect to the other cells that did not encounter the edge, demonstrating that a single P-selectin edge could be used to substantially change the direction of cell rolling and hence control the transport of rolling cell.

Figure 14:
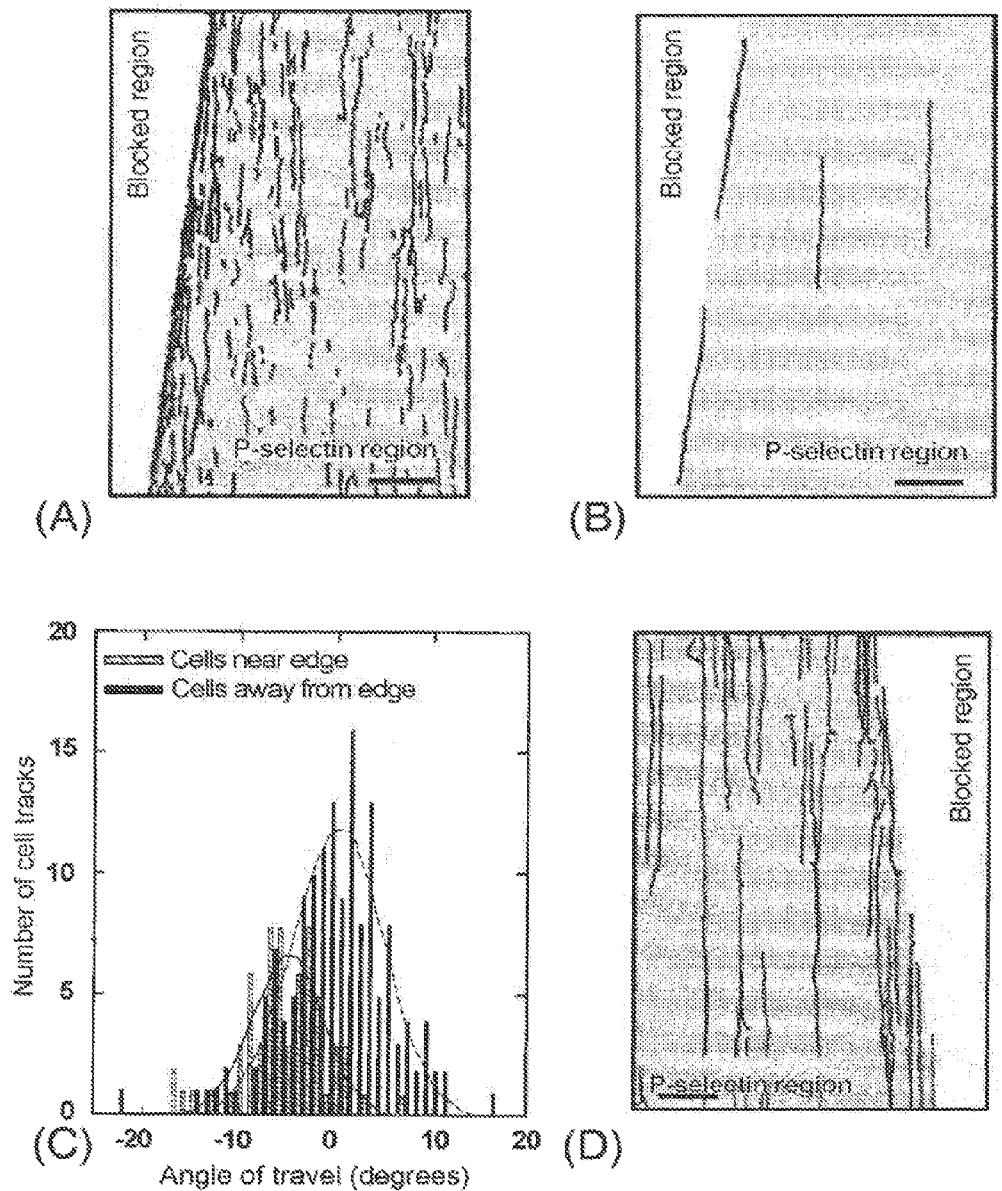
FIG. 14 shows results from analyses of cell and microsphere rolling. (A) Matlab tracking of rolling cells generated from a set of 236 images clearly shows the effect of the edge. Inability of cells to cross over the edge resulted in higher density of tracks at the edge. Cell rolling was observed in the P-selectin coated region (pink) but not in the blocked region (white). Scale bar: 300 μm. (B) Longer (>300 μm) tracks of cells rolling on the edge and inside the P-selectin region clearly show that the edge affected the rolling direction. Scale bar: 300 μm. (C) Angular distribution histogram of the direction of travel of cells rolling near the edge (red) with respect to those away from the edge (blue). Wall shear stress was 1.9 dyn/cm2 (0.19 Pa, 300 μL/min). (D) Similar experiments done with 9.96 μm diameter sLex coated microspheres that roll on P-selectin reveal that the edge did not have a large effect on microspheres as their direction of travel did not change substantially. Wall shear stress was 0.33 dyn/cm² (0.03 Pa, 200 μL/min).

To analyze the rolling behavior of the cells, the sequence of images was processed using Matlab. Statically adhered cells were filtered out and tracks of individual cells were plotted, clearly showing the different travel directions of cells rolling on the edge and those rolling inside the P-selectin region (FIG. 14A). The image acquisition rate and processing parameters were set so that only those cells that rolled on the surface were tracked. Cells that did not roll moved rapidly as compared to cells that rolled, and their large displacements per frame made it impossible to track rolling and free-flowing cells simultaneously. Tracks are not visible in the blocked region, reflecting that none of the cells rolled in that region. Cells rolling in the P-selectin region that encountered the edge were forced to roll on it instead of crossing over beyond the edge, leading to an accumulation of moving cells being transported at an angle to the fluid flow. This effect is evident in the plotted tracks (FIG. 14A) but not obvious in the images (FIG. 14) because of statically adherent cells that accumulated over a period of time. The effect of the P-selectin edge is very clear when only longer cell tracks are plotted (FIG. 14B).

To elucidate the effect of the edge on cell rolling, tracks were divided into two sets: (a) tracks that began within a distance of 30 µm from the edge (cells that encountered the edge), and (b) tracks that began beyond a distance of 90 µm of the edge (cells that were not influenced by the edge). The direction of travel of each track was identified and plotted as a histogram (FIG. 14C), with zero angle corresponding to the mean direction of cells rolling in the P-selectin region. Direction of travel of cells that encountered the edge clearly differed from the mean direction of travel of the other cells by 4-10°. This analysis further confirmed the ability of the edge to control the direction of travel of rolling cells. Furthermore, cells near the edge rolled at an average velocity of approximately 1 µm/s, whereas cells away from the edge rolled at an average velocity of approximately 0.5 µm/s. These results demonstrate that the P-selectin edge enabled control over the transport of rolling cells by (a) changing the direction of rolling and (b) increasing the rolling speed.

Similar experiments were performed with Sialyl Lewis(x) (sLex) coated microspheres that form transient bonds with P-selectin and are used as models to study cell rolling. Microspheres rolled selectively on the P-selectin region with average velocity of about 3-4 µm/s at a flow speed of about 200 µL/min, corresponding to a shear stress of about 0.33 dyn/cm2 (0.033 Pa). This velocity is in agreement with the inventors' previously acquired data on sLex coated microspheres rolling on P-selectin. Nevertheless, the P-selectin edge did not have a significant effect on the direction of rolling of the microspheres. Almost all microspheres that encountered the edge crossed over beyond the edge and their direction of travel remained unchanged (FIG. 14D). Tracks corresponding to these microspheres terminated at the edge instead of following it. Once the microspheres detached from the edge, they continued flowing in the direction of fluid flow and were no longer tracked due to their much higher speeds.

Figure 15:
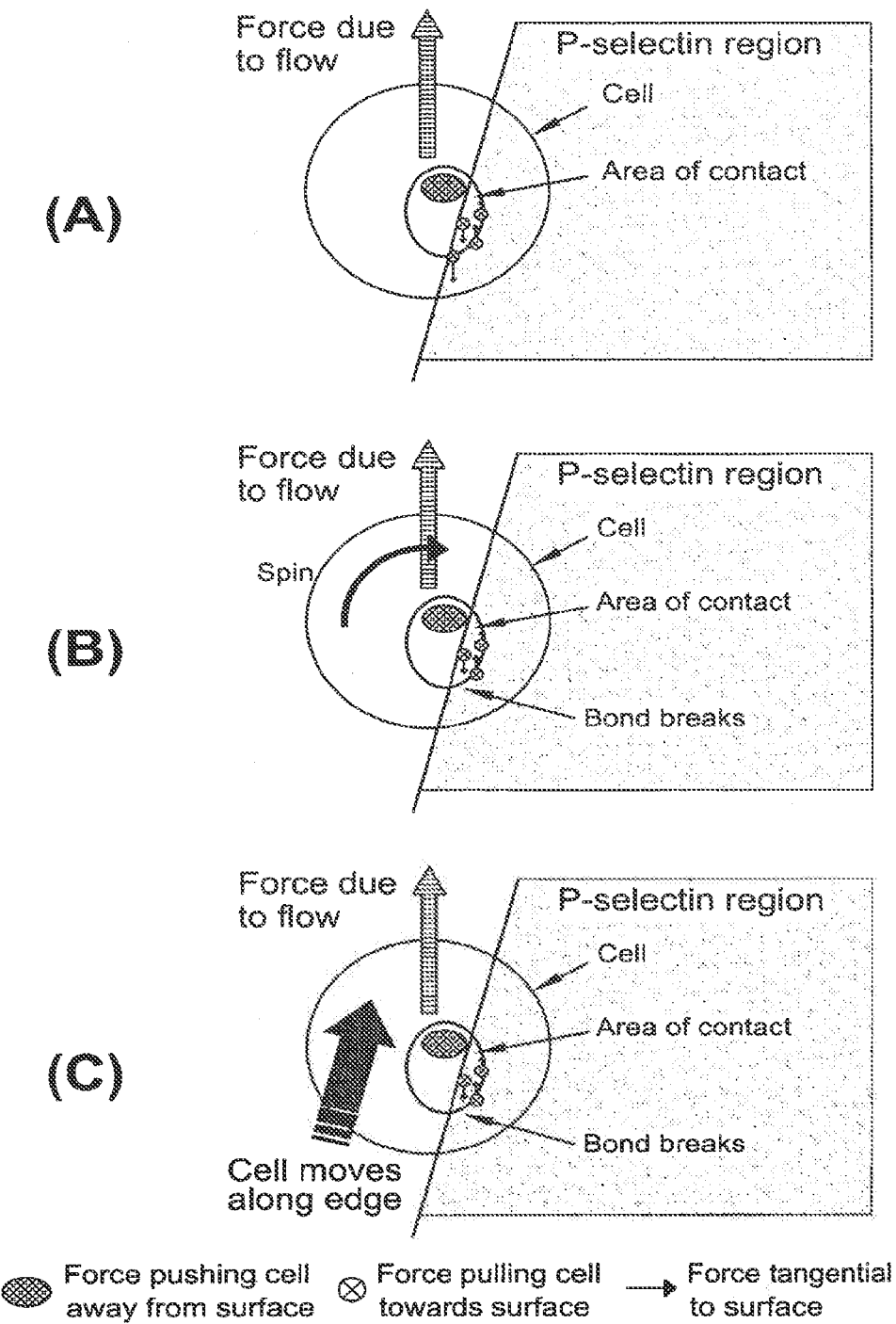
FIG. 15 illustrates a potential mechanism of cell rolling along a selectin edge. (A) Bonds on the trailing edge experience maximum strain. When these bonds break, it results in an asymmetric rotation of the cell (B) that causes the cell to move along the edge (C). This mechanism is similar to cell rolling on a surface, but in addition to rotation along an axis parallel to the surface, the cell may also spin in plane along an axis perpendicular to the surface as shown in (B). In the case of a rigid microsphere, the area of contact is small and the force due to the flow acts through a point vertically above the area of contact and this asymmetric motion becomes difficult.

This observation demonstrates that two types of particles that exhibit similar rolling behavior on P-selectin coated surfaces can exhibit dramatically different rolling behavior on P-selectin edges. This remarkable difference between the rolling behavior of cells and microspheres at the edge is not evident in one-dimensional rolling and suggests that the edge effect is capable of differentiating rolling particles based on their nanomechanical properties. It is proposed, without being held to theory, that when a cell encounters the edge, an offset between the net force acting on the cell due to fluid flow and forces exerted as the adhesive bonds dissociate cause the cell to undergo asymmetric rolling motion and follow the edge (FIG. 15). The moment driving the rolling motion in the direction of fluid flow may be expected to be of the order of $F_{drag} \times a$, where $a$ is the radius of the cell or microsphere and $F_{drag}$ is the fluid force acting on the cell. The asymmetric moments that cause the cell to follow the edge may be expected to scale as $F_{drag} \times l_{contact}$, where $l_{contact}$ is the length scale of the contact area within which the cell or microsphere interact with the substrate. This asymmetric moment may be expected to vanish if the area of contact is very small because the net force acting on the cell or microsphere would be aligned with the force due to the adhesive bonds, i.e., $F_{drag} \times l_{contact}$ would not be large enough to sustain this asymmetric motion but $F_{drag} \times \alpha$ would remain relatively unchanged. For the rigid microspheres, the contact length is limited to ~0.4-~0.6 m, assuming that either the bonds or linking molecules can extend by about 5 to about 10 nm. Nevertheless, cell rolling may depend on the mechanical properties of the cell, including its deformability and the size and extensibility of microvilli, and the contact length can be several micrometers long for rolling HL-60 cells. Furthermore, rolling cells can extend long tethers due to extension of microvilli to several micrometers that effectively increases the area of interaction between the rolling cell and the substrate. Without wishing to be bound by any particular theory, the lack of ability to extend long tethers may be why sLex coated microspheres selectively rolled on the P-selectin region but did not follow the edge even when it made a small angle with the direction of fluid flow.

This Example demonstrates that the transport of cells based on specific receptor-ligand interactions can be controlled in a label-free manner by the arrangement of receptors that mediate cell rolling. A single edge of P-selectin was capable of substantially changing the trajectory of rolling HL-60 cells with respect to the direction of fluid flow in which the cells would otherwise roll; at the same time, a single edge of P-selectin affected rolling microspheres to a much lesser extent.

Example 4

Microfluidic Device

Figure 16:
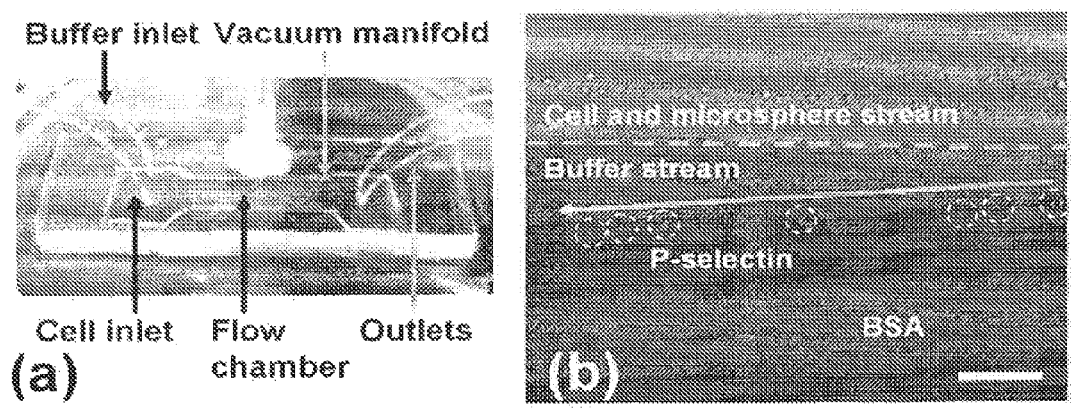
FIG. 16 depicts (A) a microfluidic device for separation of cells by rolling along receptor edges with a flow channel height of 30 μm. (B) A stream of assorted fluorescent microspheres (~2-30 μm diameter) and HL-60 cells and a buffer stream was injected into the device that contained arrangements of P-selectin at an angle to the fluid stream. Rolling HL-60 cells were selectively diverted and separated away from the microspheres in original stream, evident in the composite fluorescence and bright field image. Dashed line outlines the boundary between the cell and microsphere stream and the buffer stream. The arrow indicates direction of cell rolling along the edge. Cells on the edge are circled. Scale bar: 100 µm.

We have developed a microfluidic device that uses rolling on an edge for separation of cells. The device was fabricated using soft lithography in PDMS (polydimethylsiloxane). First, microfluidic patterning (Delamarche, E. et al. 1997. "Patterned delivery of immunoglobulins to surfaces using microfluidic networks." *Science*. 276(5313): 779-78, the entire contents of which are hereby incorporated by reference in their entirety) was used to define lines of P-selectin on a glass or polystyrene substrate. The device was then assembled using a vacuum manifold to hold the PDMS component on the substrate to form a flow chamber with height ranging from 30 μm to 250 μm (FIG. 16). The device contained separate inlets for cell and buffer streams. This arrangement permits a parallel flow of a cell stream along with a buffer stream that does not contain any cells.

As a proof-of-concept for cell separation, we examined whether the P-selectin arrangements in the device were able to nudge cells out of the cell stream by guiding cell rolling along the P-selectin edges. When a stream containing HL-60 cells and microspheres and a buffer stream were flowed through the device, some of the cells in the cell stream tethered and rolled on the P-selectin edges on the substrate. Due to the angle that the edges made with respect to the flowing cell stream, these cells were nudged out of the cell stream and were thus separated out from microspheres in the original flow stream (FIG. 16B). This result further demonstrates feasibility of creating a cell separation device based on cell rolling.

Example 5

Characterization of Mesenchymal Stem/Progenitor Cell (MSPC) Rolling on Substrates Comprising Edges In this Example, the effect of P-selectin arrangement on the rolling direction of MSPCs with respect to the direction of fluid flow is investigated. A goal of this experiment is to maximize the ability of the arrangements to direct trajectories of rolling cells and to investigate how it depends on cell properties such as size, ligand density, and deformability.

Rolling experiments are performed in a standard commercially available flow cell (Glycotech Inc.) using a glass slide (substrate) with selectin edges. MSPCs with cytoplasmic expression of GFP are used. Cells are maintained in Lonza MSPC expansion media as specified by the manufacturer. To ensure MSC identity, MSCs are characterized by flow cytometry using a variety of positive and negative cell markers (Dimitroff, C J. et al. 2001. "CD44 is a major E-selectin ligand on human hematopoietic progenitor cells." *Journal of Cell Biology*. 153(6): 1277-1286; Pittenger, M. F. 1999. "Multilineage potential of adult human mesenchymal stem cells." *Science*. 284(5411): 143-7; and Caplan, A. I. 1991. "Mesenchymal stem cells." *J Orthop Res*. 9(5): 641-50; the entire contents of each of which are hereby incorporated by reference in their entirety). Positive markers include CD90, CD146, CD44, and CD29. Negative cell markers include two specific hematopoietic cell surface markers including CD45 and CD34. Cells are incubated for 10 minutes in non-enzymatic cell dissociation solution (Sigma). After washing with PBS containing 1% FBS and 0.05% $NaN_3$ (FACS buffer), cells are filtered using a 40 μm cell strainer and incubated for 30 minutes using the following mouse IgG,κ antibodies: 1) CD34 fluorescein isothiocyanate (FITC) conjugated antibody (diluted with FACS buffer), 2) CD45 FITC-conjugated antibody, 3) CD90 FITC-conjugated antibody 4) CD146 R phycoerythrin (R-PE) conjugated antibody, 5) CD44 FITC-conjugated antibody (Abcam ab30405), and CD29 PE-conjugated antibody (FAB17781P R&D Systems), CXCR4 (R&D Systems, FAB173P).

MSPCs are also characterized for expression of P-selectin moieties using P-selectin containing the Fc region. In addition, the ability of the cells to differentiate is verified using CFU-F and CFU-O assays. (See Example 7). To ensure multi-lineage differentiation potential of MSCs, adipogenic differentiation is also examined with the adipogenic SingleQuot kit from Lonza, followed by Oil Red O staining and FACs analysis with FABP4 antibody (AF3150, R&D Systems). Images are acquired using a Nikon TE2000U microscope and analyzed using Matlab as in other work described herein. Specific covalent chemistry is used to immobilize P-selectin on a substrate previously patterned with gold. This approach is chosen for the advantages of covalent chemistry over physisorption, as well for repeatability, robustness and control as compared with other approaches such as microfluidic patterning and microcontact printing.

Thin (~10 nm) layers of gold are evaporated on glass slides and patterned using standard lithography techniques. A 10 nm gold film is chosen to facilitate visibility of cell rolling through the gold film (Mrksich, M. et al. 1996. "Controlling cell attachment on contoured surfaces with self-assembled monolayers of alkanethiolates on gold." *Proceedings of the National Academy of Sciences of the United States of America*. 93(20):10775-10778, the entire contents of which are hereby incorporated by reference in their entirety). Following gold evaporation, glass slides are treated with PEO-silane (2-(methoxy(polyethylencoxy)propyl)trimethoxysilane, Gelest, Inc.) in order to block adsorption of P-selectin on glass surfaces. P-selectin is then immobilized on gold surfaces using thiol chemistry. On gold-coated regions, oligo(ethylene glycol) (OEG)-containing alkanethiols are first conjugated to prepare non-fouling self assembled monolayers (SAMs). To control density and orientation of P-selectin, mono- and bi-functional OEG-alkanethiols are employed. For example, by changing mixture ratios between $SH$—$(CH_2)_m$—$(CH_2O)_n$—$OH$ and either $SH$—$(CH_2)_m$—$(CH_2O)_n$—$COOH$ or $SH$—$(CH_2)_m$—$(CH_2O)_n$—$NH_2$, density of reactive sites (—COOH or —$NH_2$) that can react with P-selectin can be controlled, resulting in controlled P-selectin density on the surface. In addition, the bifunctional OEG-alkanethiols is further reacted with a linker such as sulfo-(succinimidyl 4-[N-maleimidomethyl]cyclohexane-1-carboxylate) (sulfo-SMCC), allowing orientation control of P-selectin. Note that P-selectin has only one cysteine residue (the 766th amino acid located on the opposite side of the adhesive site) that contains thiol groups, which permits control over the orientation of its adhesive amine terminus (Fujimoto T. et al. 1993. "P-selectin is acylated with palmitic acid and stearic acid at cystein-766 through a thioester linkage." *Journal of Biological Chemistry*. 268(15):11394-11400). The entire surfaces are then blocked with a 5% solution of FBS in 1×PBS.

Determination of P-Selectin Edges that Maximize Deflection of Rolling Cells

A basic arrangement comprising strips of selectin defined by width of selectin strip ($w_s$), width of gap ($w_g$), and angle with respect to flow direction ($\alpha_s$) (FIG. 5) will be used. Minimum pattern dimension (~0.5 μm) is determined by lithography resolution. Preliminary data indicate that, under the conditions of these particular experiments, cells are unable to be directed by an edge for large $\alpha_s$. Nevertheless, it is expected that the use of multiple edges may have a significant effect on the trajectory of rolling cells even at large $\alpha_s$. $\alpha_s$ will therefore be varied between about 1° and about 60°.

The area of contact of a rolling cell with the substrate and the distance traveled by a cell before reattachment to the substrate may be two parameters that are particularly relevant to the design of $w_s$ and $w_g$. Prior studies on cell rolling suggest that the area of contact is typically in the range of about 5 to about 10 μm (Dong, C. et al. 2000. "Biomechanics of cell rolling: shear flow, cell-surface adhesion, and cell deformability." 33(1):35-43, the entire contents of which are hereby incorporated by reference in their entirety). $w_g$ will be varied between the minimum size determined by lithography resolution (~0.5 μm) and about 10 μm, which may be an upper limit for contact dimension. Without wishing to be bound by any particular theory, the distance traveled by a cell that detaches from an edge before reattachment should be minimized for the most effective separation. For $w_s<w_g$ the fraction of substrate coated with selectin is small, and reattachment kinetics may be adversely affected. Nevertheless, increasing $w_s$ beyond $w_g$ gives diminishing returns, as most of the surface becomes covered with selectin and the number of edges is reduced. An edge arrangement will therefore be set with width $w \equiv w_s = w_g$. Edges will be designed such that several combinations of $\alpha_s$ and $w$ can be tested on a single glass slide in a single experiment.

Trajectories are obtained for MSPCs rolling on each arrangement for different values of $\alpha_s$ and $w$. Width ($w = $gap width $w_g$ and selectin width $w_s$) is varied as 0.5, 1, 2, 5, and 10 μm. Edge angle $\alpha_s$ is varied as 1°, 2°, 5°, 10°, 20°, 40°, and 60°. For each width, the maximum trajectory angle $\alpha_{tr}$ at which cells can be made to roll with respect to flow direction will be determined. In addition, the distance traveled by the cells while rolling along the edge is quantified using Matlab as in work described herein. It is expected that the maximum trajectory angle will become independent of the width (w) if the width is larger than the area of contact of the cell with the substrate. The angular distribution of cell trajectories are also evaluated for each selectin arrangement. (See the similar to the evaluation shown in FIG. 14). In addition to geometry of coated areas and edges, the effect of P-selectin density is determined by decreasing the density of P-selectin and observing its effect on the maximum trajectory angle $\alpha_{tr}$.

Investigation of Effects of Cell Size and Deformability on the Ability of Substrates Comprising Edges to Direct Trajectories of Rolling Cells Biomechanical properties of MSPCs may be expected to play a role in cell rolling and homing processes. The effect of cell size and cell deformability is investigated by controlling each parameter independently. Without wishing to be bound by any particular theory, cell deformability may play an important role, since rolling along an edge was not observed in the case of rigid microspheres even for small $\alpha_s$. Cell size affects the area of contact and also affects the shear force exerted by fluid flow on the cell. In order to study the effect of cell size, MSPCs are sorted according to cell size by flow cytometry into 3-4 subpopulations containing more homogeneous size distributions. Cell deformability is controlled by treating the cells with cytochalasin D, which increases cell deformability. Cytochalasin D is a cell permeable mycotoxin, which causes both the association and dissociation of actin subunits. Cytochalasin D disrupts actin filaments and inhibits actin polymerization, resulting in disruption of cytoskeleton. Since cytochalasin D will also interfere with the cell's ability to produce pseudopod extensions to interact with the substrate, an alternative, methyl-β-cyclodextrin (MβCD) is also employed to decrease cell rigidity. MβCD is known to deplete cholesterol from cell membranes, resulting in a substantial increase in membrane fluidity.

To determine the effect of cell size and deformability on rolling behavior, rolling experiments are repeated for specific MSPC subpopulations. To study the effect of cell size, maximum trajectory angle $\alpha_{tr}$ is determined for 3-4 subpopulations of MSPCs sorted on the basis of cell size. Similarly, the effect of cell deformability is determined by observing how cytochalasin D (or MβCD) affects the maximum $\alpha_{tr}$.

Example 6

Enrichment of Supopulations of MPSC by Rolling on P-Selectin

This Example demonstrates separation of a population of cells into subpopulations using methods and devices of the present invention.

MSPCs are separated into 3-4 subpopulations by rolling and differences (such as, for example, size and receptor density) between resulting subpopulations is examined using flow cytometry. Separation is achieved by design and fabrication of a microfluidic device based on cell rolling characterization of Example 5. It is expected that the cells are separated on the basis of size, ligand density, cell deformability, or combinations thereof.

Device Design

Devices comprise an inlet for cell suspension, another inlet for buffer/medium, a separation flow chamber, and several outlets (FIG. 3). Results from Example 5 are used to guide design of geometry of the device and of selectin arrangements. The cell suspension inlet width is kept to ~30 µm, as increasing this width would likely increase the separation distance and thereby increase the time required for cells to flow through the device. Edges of selectin are designed based on the maximum trajectory angle $\alpha_{tr}$ determined for each cell population in Example 5. Examples of designs that are contemplated include (a) constant edge angle, and (b) varying edge angle (FIGS. 3A and 3B).

Choice of edge and coated area designs are influenced by the sensitivity of cell trajectories to the design: if, for a design that maximizes at, for a particular subpopulation, $\alpha_{tr}$ is very small for other subpopulations, a varying edge angle design may be suitable. A constant edge angle design may be suitable for other situations. The minimum length of the flow chamber is given approximately by $$L \sim \frac{w_{inter} N}{\tan(\alpha_{max})} \quad \text{Eq. 3}$$

where N is the desired number of fractions. For $w_{inlet}=30$ µm, N=4, and $\alpha_{max}=8°$, the minimum length of the flow chamber is about 850 µm. Cell separation time is 5-10 min for typical rolling speeds observed in our experiments for this geometry. Since cell rolling is inherently slow, parallel device operation may be necessary for sufficient throughput. For physiological shear stress of 10 dyn/cm$^2$, the cell suspension inlet flow rate is calculated to be approximately 1 µL/min. A goal is to separate approximately $10^5$ cells in 100 µL at a cell density of $10^6$/mL. Ten devices are employed in parallel to separate cell suspension at a rate of 10 µL/min (FIG. 3).

Device Fabrication

Devices are fabricated from PDMS (polydimethylsiloxane) (Sylgard 184, Dow Corning) using a standard micromolding process on a SU-8 (photocurable epoxy from Microchem, Inc.) master mold. SU-8 patterns with connecting microchannels with the desired height will be fabricated on 4" silicon wafers using standard procedures, followed by silane treatment to prevent PDMS sticking to the molds. A mixture of PDMS and curing agent in the ratio 10:1 by weight is poured on the master and cured at 60° C. for 1 hour. After curing, the PDMS components will be peeled off and access holes will be punched for inlets and outlets. A second layer of PDMS with connecting manifolds is similarly fabricated and bonded to this layer using oxygen plasma treatment. Inlet and outlet tubing are connected to this layer using silicone adhesive. PDMS components are placed on other glass slides previously coated in some areas with selectin for experiments. PDMS components and glass slides are held together using a mechanical clamp or vacuum.

Separation of MSPCs

MSPCs are characterized for P-selectin density at different passage numbers by FACS analysis to examine the variation of ligand expression with passages. P-selectin labeled with FITC using an Antibody Labeling Kit (53027, Pierce) according to the manufactures protocol will be used for this characterization. MSPCs at a density of $10^5$-$10^6$ cells/mL and buffer or cell culture medium are flowed into the device at flow rates of 10 µL/min and 30 to 100 L/min (depending on device geometry), respectively. Three to five subpopulations are collected and analyzed for (a) cell size, (b) ligand density, and (c) deformability. Cell size and P-selectin ligand density are characterized for each subpopulation using BD FACS Calibur as described above. Cell deformability is assessed by forcing cells to enter narrow microfluidic channels under a controlled pressure drop and observing the time it takes a cell to enter a channel. To better understand the differences between the separated subpopulations, a statistical model is constructed to correlate the effect of size, deformability, and ligand density on MSPC receptor expression profile and on ability to form CFU-Fs (Example 7). This model is useful to tune design parameters for enhanced separation and help determine whether cell rolling can be used to separate MSPCs based on specific properties.

Example 7

Identification of MSPC Subpopulations with Enhanced Differentiation and Cell Migration Potential The present Example illustrates another potential use of cell separation systems disclosed herein. Differentiation and migration potential of MSPC subpopulations such as osteogenic lineage cells are examined.

It is expected that rolling-based separation of MSPCs will yield subpopulations that exhibit different capacities to differentiate (measured, for example, by ability to form colonies and produce bone matrix) and/or differences in migration behavior.

The osteogenic lineage provides an attractive functional assay which can be used to effectively assess the number of progenitors within a population of cells. Bone nodules are each initiated by a single MSPC and are produced during de novo bone formation on a solid surface. De novo bone formation is initiated by differentiating osteogenic cells and is marked by the presence of a cement line matrix.

The sequence of bone formation in vitro parallels that of intramembranous bone formation during embryogenesis and endosseous wound healing and has been demonstrated for a variety of species including rat and human and for osteogenic cells derived from human embryonic stem cells (Davies, J. E. et al. 1991. "Deposition and resorption of calcified matrix in vitro by rant marrow cells." *Cells and Materials*. 1(1):3-15; Baksh, D. et al. 2003. "Adult human bone marrow-derived mesenchymal progenitor cells are capable of adhesion-independent survival and expansion." *Exp. Hematol*. 31(8):723-32; and Karp et al. 2006 (cited herein); the entire contents of each of which are hereby incorporated by reference in their entirety). The extracellular matrix produced by osteogenic cells is assembled into discrete islands of mineralized matrix called bone nodules. Through retrospective analysis of bone nodule numbers normalized to input cell numbers, one can indirectly determine the number (frequency) of recruited MSPCs (osteoprogenitors). Bone marrow contains approximately 1 in 10,000 to 1 in 100,000 MSPCs per adherent cell; this number decreases with age after reaching its peak in the mid to late 20s in humans. Although there is considerable interest in culture expanding MSPCs, the rate of expansion and the yields of MSPCs are inversely related to the plating density and incubation time of each passage.

The ability to enrich and/or isolate populations of osteoprogenitor cells (i.e., progenitor cells that have the capacity to form bone nodule, in some cases, after a migration event in response to stromal derived factor-1 (SDF-1)) would serve as a proof of concept for edge-based cell rolling separation technologies.

As a control experiment, separated MSPC subpopulations are also examined by FACS analysis to determine whether there are any differences in expression of known MSPC markers CD45, CD90, CD44, and CD29 as described in Example 5.

Characterization of Expression of MSPC Homing Receptor (CXCR4) on Separated Subpopulations MSPCs lack or have highly variable cell surface expression of many of the key cytokine receptors and integrins that are responsible for homing of leukocytes and hematopoetic stem cells such as the stromal derived factor-1 (SDF-1) receptor (CXCR4). Methods of improving trafficking and engraftment of MSCs and other cell types are a high priority for cellular therapies. Retrovirus vectors encoding homing receptors such as CXCR4 have been recently used to enhance homing and engraftment of HSCs and MSCs through increasing cell invasion in response to stromal derived factor-1 (SDF-1), the ligand for CXCR4, which is typically present at inflammatory sites. A more suitable alternative would be to separate MSPCs that express CXCR4 without labeling the receptors (as required in FACS sorting).

To examine whether CXCR4 positive cells exhibit different rolling behavior, rolling of MSPCs that express CXCR4 (obtained by FACS sorting) is compared with rolling of MSPCs those that do not express CXCR4. Since CXCR4 is not a known rolling receptor, it is anticipated that CXCR4 antibodies will not affect cell rolling. If CXCR4-expressing cells exhibit different rolling behavior, cells that express CXCR4 are separated from those that do not express CXCR4. MSPCs are separated into subpopulations and expression of CXCR4 in each subpopulation are examined to evaluate whether label-free separation of CXCR4-expressing MSPCs can be achieved using cell rolling separation systems disclosed herein.

Determination of the Ability of the Isolated Subpopulations to Migrate in Response to SDF-1

In addition to differences in the number of isolated osteoprogenitors, subpopulations of MSPCs may have different capacities to transmigrate through the vascular endothelium into the target tissue. It is believed that MSPC transmigration is mediated via interactions between the CXCR4 receptor, which is expressed on a subpopulation of MSPCs, and its ligand SDF-144 which is similar to the homing mechanism of hematopoetic cells. To determine if isolated fractions exhibit different potentials to undergo a migration event followed by bone nodule production, a modified Boyden chamber assay is employed as previously described (Karp et al. 2005). Approximately 50,000 isolated cells from each fraction will be added to transwell filters placed into the wells of 6-well plates. Cells are allowed to adhere for 10 hours in the presence of 15% FBS, after which wells are rinsed with PBS. Following the addition of 10 or 100 ng/ml of SDF-1 to the lower compartment, cells are incubated for 24 hours and then cells on top of the filter are removed with a cotton swab. After rinsing the upper and lower compartments with PBS 3 times, CFU-O media is added to the upper and lower compartments. Cells are incubated for an additional 2-3 weeks with media changes every 2 or 3 days. Areas containing mineralized regions are quantified using tetracycline (Karp et al. 2005).

To determine the numbers of cells on the underside of the filters prior to switching to CFU-O media (i.e. total numbers of cells that migrated from each fraction in response to SDF-1), cells on the tops of some filters are removed by scraping with a cotton swab. Whole filters are then stained with toluidine blue and then observed under a light microscope.

Quantification of the Number of Bone Nodules from Separated Subpopulations

The differentiation potentials of subpopulations obtained by rolling-based separation are quantified and compared to that of subpopulations obtained by FACS based on P-selectin ligand density. For FACS separation, P-selectin with Fe region are used. Three to four subpopulations of MSPCs are separated using BD FACS Calibur based on P-selectin ligand density.

The number of osteoprogenitors is quantified using a colony forming unit osteoblast (CFU-O) assay (Karp et al. 2005). To stimulate differentiation into osteogenic cells, media containing α-MEM and FBS is supplemented with $10^{-8}$ M dexamethasone (DEX), 50 μ/ml ascorbic acid (AA), and 5 mM Beta glycerophosphate (βgP) together with antibiotics and fungizone. Through its interaction with specific glucocorticoid receptors, DEX has been demonstrated to stimulate osteogenic differentiation for progenitor cells derived from multiple tissues. AA facilitates collagen assembly and βgP facilitates mineralization of the collagen. Media will be changed every 2-3 days and mineralized areas are observed by light microscopy and by electron microscopy. Cultures are treated either with or without osteogenic supplements to assess directed versus spontaneous differentiation into osteogenic cells, respectively.

To examine the number of colony forming unit fibroblasts (CFU-Fs) (a functional assay for MSPCs), cells are cultured as described by Castro-Malaspina et al. 1980. "Characterization of human bone marrow fibroblast colony-forming cells (CFU-F) and their progeny." *Blood.* 56(2):289-301, the entire contents of which are hereby incorporated by reference in their entirety). A positive CFU-F colony is identified as an adherent colony containing more than 50 cells that is α-naphthyl acetate esterase-negative and hematoxylin & eosin-positive (Baksh, D. et al. 2003). The CFU-F assay for colony forming potential provides a rough estimate for the number of MSPCs in each fraction. CFU-F in addition to CFU-O analysis provides pertinent data regarding the potential of the MSPCs in each fraction.

Examples 8-10

Systems for Separating and Detecting Activated Neutrophils

This year, hundreds of thousands of infants world-wide will develop sepsis, a result of the body's inflammatory response to an infection, which can lead to organ failure and death. Mortality may be as high as 50% for infants who are not treated, with almost half of the sepsis-related deaths occurring among infants who are born prematurely. Most sepsis detection systems rely on identification of blood plasma levels of certain factors or blood cultures that require a centralized laboratory, or on clinical symptoms that are not specific. Outcomes for negative blood cultures typically require 5 days, which is often too late to affect therapeutic decision. A simple method to quickly detect sepsis at the point-of-care would enable required medical treatment to be administered on time, greatly reducing infant mortality.

Recent research indicates that expression of CD64 on neutrophils is a highly specific biomarker for neonatal sepsis that is not significantly affected by conditions such as fever or chemotherapy (Bhandari, V. et al. 2008. "Hematologic profile of sepsis in neonates: neutrophil CD64 as a diagnostic marker." 121(1): 129-134 and Ng, P. 2002. "Neutrophil CD64 expression: a sensitive diagnostic marker for late-onset nosocomial infection in very low birthweight infants. *Pediatric Research.* 51(3): 296-3-3.) Although enzyme linked immunoabsorption assays (ELISAs) and flow cytometry techniques are useful for examining CD64 levels on neutrophils, these techniques require extensive sample processing, and proper storage conditions, and are typically not amenable for point-of-care diagnostics.

Figure 17:
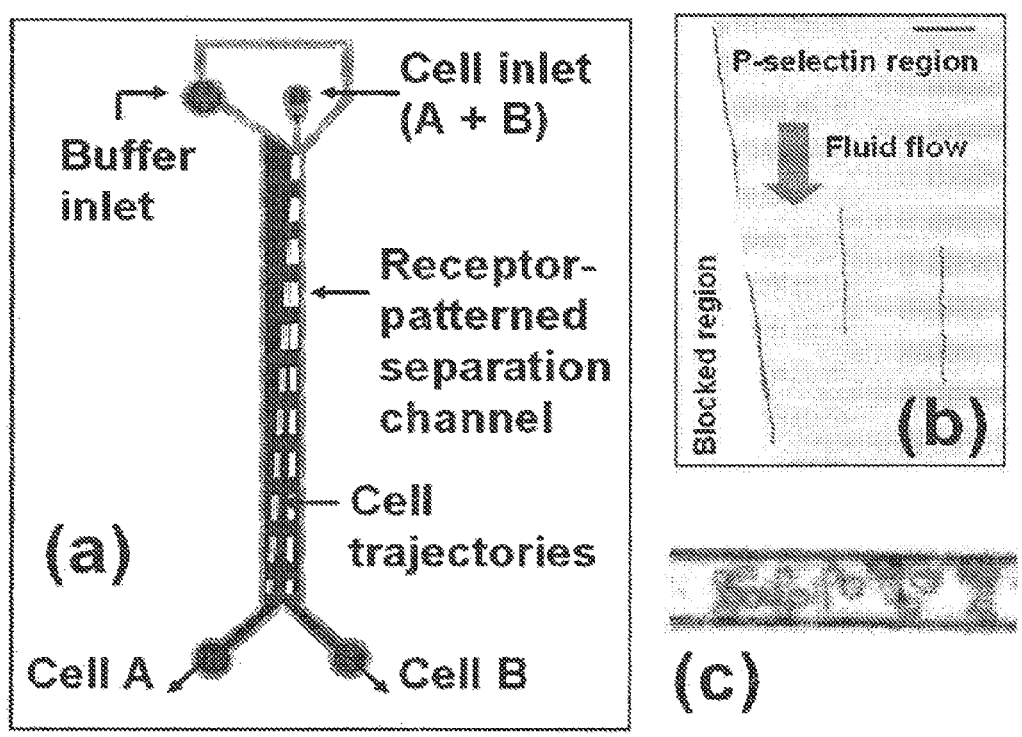
FIG. 17 depicts (A) a design of micro-device. (B) HL-60 cell rolling tracks show control of rolling using edges of P-selectin coated areas (pink). (C) Cells within collection channels observed with low power microscope.

Inventive methods for directing the trajectories of rolling cells using asymmetric arrangements of receptors (as described herein) could be harnessed to separate and detect activated CD64 expressing neutrophils for rapid, label-free diagnosis of sepsis. For example, a device for cell rolling with a design such as that shown in FIG. 17A might be useful for separating and detecting activated CD64+ neutrophils from other cells.

We have also developed techniques for covalent immobilization of selectins and antibodies such as CD64 that allow for arrangement and control over surface density and orientation of the selectins, as well as prolonged shelf life. This approach can be used for enhanced control of the rolling response of sLex ligand bound microspheres and live neutrophils compared to physisorption. The substrates provided by the present Example are directed toward a goal of developing a simple, stand-alone device based on cell rolling for rapid separation and detection of neutrophils that express CD64 on a timescale of minutes, without any processing steps.

Without wishing to be bound by any particular theory, properties of rolling cells appear to depend on cell size, receptor expression, and cell deformability. It is therefore hypothesized, again without wishing to be bound by any particular theory, that activated neutrophils expressing CD64 can be separated from other cell types within whole blood. The following Examples are expected to demonstrate separation of activated neutrophils from non-activated neutrophils with high specificity. These methods can then be used to effectively separate CD64 neutrophils from whole blood.

Example 8

Development of P-Selectin and Anti-CD64 Antibody Co-Immobilized Substrates

Figure 18:
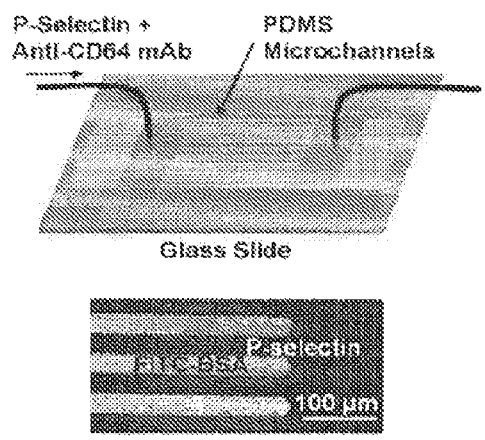
FIG. 18 illustrates how microfluidic arrangements of biomolecules can be achieved by flowing the biomolecules through PDMS microchannels reversibly bonded to a substrate. This technique has been used to create P-selectin edges and the design has been visualized by exposure to fluorescently labeled BSA following the arranging step. BSA selectively adsorbs on the region without P-selectin and appears bright.

In the present Example, substrates useful for detecting activated neutrophils are developed. Such substrates comprising a mixture of cell adhesion molecules (in this Example, P-selectin) and antibodies for a marker expressed by activated neutrophils (in this Example, CD64).
Coating Surfaces P-selectin and anti-CD64 antibody will be coated onto surfaces such that edges are created between coated areas and uncoated areas using microfluidic patterning (FIG. 18). In this technique, microfluidic channels in polydimethylsiloxane (PDMS) are reversibly bonded to a glass slide, and the desired receptor solution is flowed through the microfluidic channel for immobilization. Microfluidic channels are prepared using SU-8 master mold and soft lithography techniques (Duffy, D. C. et al. "Rapid prototyping of microfluidic systems in poly(dimethylsiloxane)." *Analytical Chemistry.* 70(23): 4974-4984, the entire contents of which are hereby incorporated by reference in their entirety).

Approximately 50 μm thick SU-8 photoresists are drawn into 50 μm wide lines that define the microchannels on a four inch silicon wafer. After processing, the mold is baked at approximately 150° C. for 15 min to smoothen the edges of SU-8. The SU-8 mold is then placed in a desiccator with a few drops of tridecafluoro-1,1,2,2-tetrahydrooctyl-1-trichlorosilane (United Chemical Technologies, Bristol, Pa.) to aid in the future removal of PDMS. Monomer and curing agent are mixed in a 10:1 ratio, poured over the mold, degassed, cured at 90° C. for 30 minutes, and then removed from the mold. Inlet and outlet holes are drilled and the PDMS microchannels are placed on the glass substrate, forming closed microchannels through which solutions can be flowed using syringe pumps. We have already demonstrated microfluidic creation of P-selectin edges on glass by physisorption (FIG. 18). For better control over the surface densities of P-selectin and anti-CD64 mAb, we are further developing this technique for covalent co-immobilization of the two receptors.
Immobilization Scheme Epoxy chemistry is used to covalently immobilize receptors on glass substrates. Epoxy-functionalized glass slides is obtained from ArrayIt Inc. and used directly for covalent immobilization without further treatment. The PDMS microfluidic component is placed on the epoxy slide and P-selectin and/or anti-CD64 mAb solutions in PBS buffer is flowed through the microfluidic channels. After immobilization, the PDMS component is peeled off and the entire surface is blocked with 5 mg/mL BSA for 1 hour.
Density Control of Co-Immobilized P-Selectin and Anti-CD64 mAb Control of surface densities of P-selectin and anti-CD64 mAb may be important for developing an optimized cell separation device. To test different densities of P-selectin and anti-CD64 mAb, their concentrations are varied in the solution during microfluidic patterning. Initial experiments use different ratios of P-selectin:anti-CD64 mAb concentrations of 1:1, 10:1, and 20:1 (with P-selectin concentrations kept at about 5 μg/mL). Total densities are varied by varying the immobilization time of the two receptors (about 5 minutes and about 1 hour) at the same P-selectin concentration to obtain low and high surface densities at the three ratios. After arrangement of the receptors, surfaces are blocked with 5 mg/mL BSA for 1 hour. Surfaces are characterized qualitatively using fluorescence measurements and quantitatively for surface density of P-selectin and anti-CD64 mAb using a radio-labeling technique as described below.
Fluorescence Characterization of P-Selectin Biotinylated sialyl Lewis(x) (sLex) is obtained from Glycotech and incubated with Alexa 488 streptavidin (Invitrogen, Inc.) in a molar ratio of 1:1 at a streptavidin concentration of 1 mg/mL in PBS. sLex is a saccharide that binds to P-selectin and is used for surface coating of microspheres that mimic cell rolling (Hong, S. et al. 2007. "Covalent immobilization of P-selectin enhances cell rolling." *Langmuir.* 23(24): 12261-12268, the entire contents of which are hereby incorporated by reference). For characterization of anti-CD64 mAb immobilization, recombinant human Fcγ receptor 1 (CD64) consisting of the extracellular domain of the Fcγ receptor is obtained from R&D Systems and labeled with Alexa 647 using a protein labeling kit (Invitrogen, Inc). Surfaces are incubated with 10 μg/mL solution of the streptavidin-sLex conjugate and 10 μg/mL Fcγ receptor overnight at 4° C. After incubation, slides are rinsed twice with 1×PBS for 10 minutes and imaged under a Nikon TE2000-U inverted epifluorescence microscope equipped with an Andor 885 camera for imaging. Fluorescence images using filters for Alexa 488 and for Alexa 647 are acquired under identical conditions and their intensities quantified to verify control over immobilization of P-selectin and Anti-CD64 mAb.

Site Density Measurements Using Radio-Labeling with Iodine ($^{125}$I)

Site densities of substrate-bound ligands are measured by radioactivity through iodinating ($^{125}$I) anti-CD64 antibody or P-selectin prior to exposure on the substrate. Radioiodination of the ligands is performed using the IODO-GEN® Iodination Reagent kit (Piercenet, IL) according to the manufacturer's protocol. Antibodies are purified prior to iodination using protein A beads (Piercenet, IL) and then iodinated using tubes coated with iodogen (typically a ratio of 10 μg or less of the IODO-GEN® Reagent per 100 μg of antibody). To prevent oxidation of the ligands, 500 μCi of carrier-free Na$^{125}$I is first added to the IODO-GEN tubes and incubated for 10-15 minutes with agitation followed by addition of the ligand solution (100 μg of purified antibody sample dissolved in 100 μL PBS).

The sample is removed from the reaction tubes to terminate the iodination of the sample by adding tyrosine-like molecules such as 4-hydroxyphenyl propionic acid or 4-hydroxyphenyl acetic acid (~50 μL of 10 mg/mL), which binds to active radioiodide. Next, the radio-iodinated ligand fraction is purified and separated from iodotyrosine and unlabelled ligands by passing through a gel filtration column (provided in the kit form Pierce). The radio-iodinated ligands are stored in buffer at 4° C. and are used fresh for each analysis to minimize loss of the radioactivity.

Radioactivity of the labeled ligands per unit mass (specific radioactivity) is measured with the gamma counter as μCi/mmol. For a given mass or concentration of antibody (as measured, for example, by a protein bicinchoninic acid (BCA) assay), it is possible to measure the radioactivity; from the molecular weight of the antibody, it is possible to calculate the amount of radioactivity per unit mass or in terms per antibody.

To determine site densities of immobilized P-selectin or anti-CD64, $^{125}$I-labeled ligands are covalently immobilized as described above. P-selectin and anti-CD64 mAb site densities are analyzed separately for each surface. Surfaces are then washed three times with PBS, 1.5 mM Ca$^{2+}$, 0.1% Triton X-100. Bound ligand are removed by 0.1 M NaOH, and radioactivity are measured using a gamma counter.

Example 9

Characterization of Neutrophils on Co-Immobilized Substrates

In this Example, the effect of edges (generated by areas coated with P-selectin and anti-CD64 mAb) on the rolling direction of neutrophils with respect to the direction of fluid flow are investigated. A goal of this study is to maximize the ability of arrangements to direct trajectories of activated neutrophils as compared to non-activated neutrophils by varying P-selectin and anti-CD64 mAb surface densities and edge angles. This study facilitates the design of a device for cell separation and helps determine relative sensitivities of the separation technique to neutrophil activation.

Rolling experiments are performed in a standard commercially available flow cell (Glycotech Inc.) using a glass slide (substrate) with co-immobilized arrangements of P-selectin and anti-CD64 mAb. Neutrophils obtained from All-Cells Inc. are kept in sterile Hanks' balanced salt solution containing 0.5% human serum albumin, 2 mM Ca$^{2+}$, and 10 mM HEPES at pH 7.4 until flow experiments are conducted as previously described (Hong et al. 2007). To activate neutrophils, 5×10$^6$ cells/mL in HBSS are incubated for 30 minutes at 37° C. with 2 nM TNF-α (pre-dissolved in PBS containing 4 mg/ml BSA). Neutrophils are flowed over the glass slide at a shear stress of about 1 dyn/cm$^2$, which is within the range of physiological shear stress. Images are acquired using a Nikon TE2000U microscope and analyzed using Matlab as in our present work.

Quantification of Site Density of CD64 Expression on Activated Neutrophils

Figure 19:
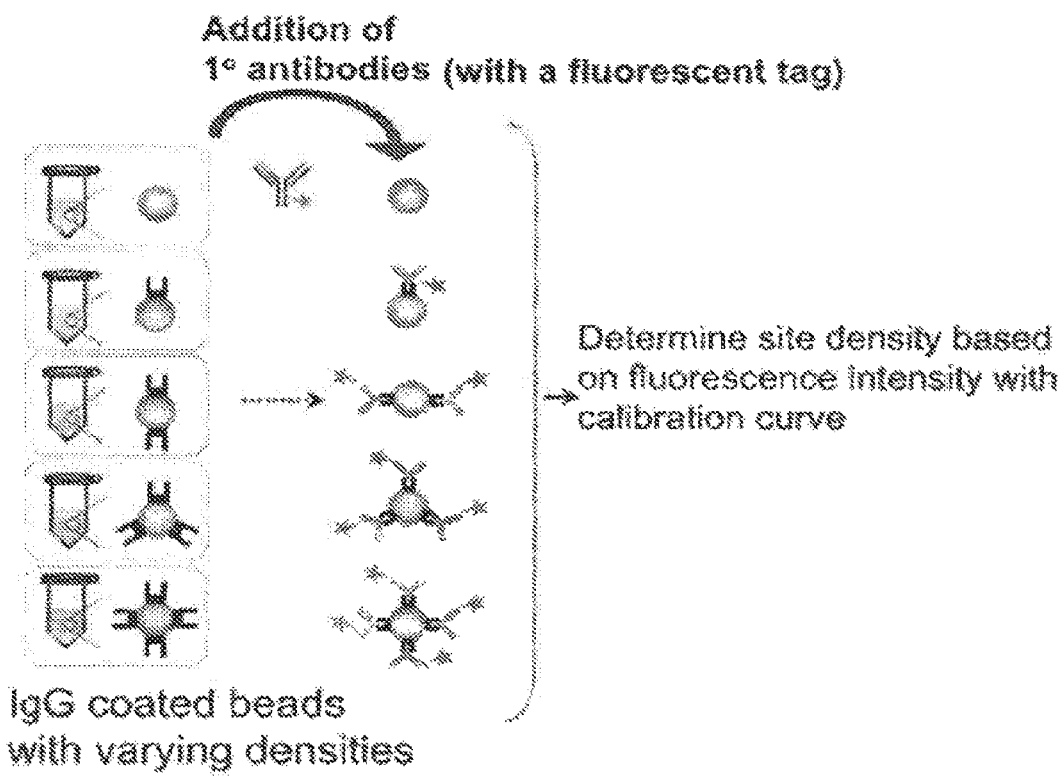
FIG. 19 depicts a schematic for site density determination of CD64 on neutrophils. To determine the site density of antibodies bound to the surface of the neutrophils, standard IgG beads will be bound to the FITC-biotin antibody and used to generate a calibration curve of site density versus fluorescence intensity as described by the supplier.

To determine the site density of CD64 on the primary human neutrophil surface, flow cytometry is performed using microbeads of specific antibody binding capacity (ABC) (Quantum Simply Cellular kit; Sigma-Aldrich) (FIG. 19). When microbeads are labeled with a specific antibody, they can serve as a set of standards to calibrate the fluorescence scale of the flow cytometer in units of ABC (number of Antibodies Bound per Cell or microbead). The Quantum Simply Cellular kit is a mixture of four highly uniform microbead populations of known antibody binding capacities. The microbeads are labeled under the same conditions as cells and with an equal amount of the test antibody as the experimental samples. Median values of the fluorescence intensity of the four peaks corresponding to the four microbead populations are used to construct a calibration curve.

Approximately 500 μL of each of the 4 IgG labeled beads (with varying densities) is added to 50 μL of the cell medium and vortexed. Approximately 10 μg/mL of anti-biotin-FITC antibody (anti-CD64, Abcam, ab34224) is incubated in the dark for 30 minutes with each of the labeled bead samples or with the cell suspension. About 2 mL of cell suspension solution is added and centrifuged at 2500×g for 5 minutes. Samples be rinsed 2 times (centrifuged at 2500×g for 5 minutes) and then placed into 500 μL of the same solution as the cells to be analyzed. Microspheres and cells are analyzed using flow cytometry. A flow rate of approximately 100-200 events per second is used with approximately 1000 events collected per bead population. Blank beads without stain serve as a negative control.

Using a forward scatter versus side scatter dot plot, a live gate around the singlet population of microspheres is constructed and the peak (median) histogram channels of each of the five populations of microspheres are determined in the corresponding fluorescent channel for entry into the Quick-Cal® spreadsheet (software available at www.bangslabs.com). Unstained cells are used as a negative control and run at the same instrument settings as the bead standards. The ABC value of the unstained cell sample is subtracted from the ABC values of the stained cell samples.

QuickCal® is used to generate a calibration curve, determine the instrument detection threshold, and quantify the ABC values of unknown samples. To establish a calibration curve, the ABC (y-axis) is plotted versus the peak channel (x-axis) for each of the 4 antibody-binding microspheres. For linear fluorescence, a log-log plot of the data should give a 45° line. For ABC detection threshold determination, after completing the ABC calibration procedure and plotting the calibration curve, the peak (median) channel of the reference blank is recorded (in some experiments the unstained cell sample is used as the reference blank). The calibration plot is then used to determine the ABC value associated with the fluorescence of the reference blank (or unstained cells). This is the ABC detection threshold of the instrument at these instrument settings. The detection threshold is the lowest number of ABC units detectable above instrument noise. For ABC quantitation of samples, after completing the ABC calibration procedure described above and plotting the calibration curve, the unknown cell samples are determined using the flow cytometer (with exactly the same instrument settings as used for ABC calibration). The sample's peak (median or geometric mean) channel value for each population will be determined and the calibration plot used to determine the ABC value that corresponds to each of the sample's peak channels. The ABC value of the unstained cell sample is subtracted from the ABC values of the stained cell samples. The cell area is determined by examining the diameter of 10 cells in suspension at 40× and used to calculate the CD64 site density.

Determining Optimal Surface Densities of P-Selectin and Anti-CD64 mAb

Rolling of activated and non-activated neutrophils are first characterized to maximize differences in their rolling behavior on a plain surface comprising co-immobilized P-selectin and anti-CD64 mAb without any angled edges. Cell suspensions at a density of approximately $5 \times 10^4$ cells/mL are flowed over the receptor-coated substrate in a flow chamber using a syringe pump at a shear rate of about 1 dyn/cm$^2$. For this study, surfaces comprising edges between coated areas and uncoated areas are not used since the goal is to analyze rolling behavior without edge effects. Cell rolling is studied separately for activated and non-activated neutrophils and analyzed using Matlab for the number of rolling cells, number of stuck cells, and rolling velocities.

Without wishing to be bound by any particular theory, it is predicted that differences in rolling behavior between activated and non-activated cells may increase as the surface density of anti-CD64 mAb is increased, affecting the rolling velocity and number of cells interacting with the surface. Nevertheless, the number of statically adherent cells may also increase at higher surface densities of anti-CD64 mAb. An intermediate value may be optimal for separation of activated neutrophils from non-activated neutrophils. The number and velocity of rolling cells are therefore be quantified as well as the number of statically adherent cells for different surface densities of P-selectin and anti-CD64 mAb (as described in Example 8). This study should identify a surface preparation with densities of P-selectin and anti-CD64 mAb that maximize differences in rolling velocity between activated and non-activated cells while minimizing number of statically adherent cells.

Determining Edge Angle to Maximize Difference Between Trajectories of Activated and Non-Activated Neutrophils After identifying the P-selectin and anti-CD64 mAb surface densities, an optimal edge angle ($\alpha_s$) is identified to maximize the separation of activated and non-activated neutrophils. A design comprising stripes of selectin/mAb defined by width of selectin strip (w) and angle with respect to flow direction ($\alpha_s$) (FIG. 5) is used. w is fixed at approximately 50 μm and the edge angle ($\alpha_s$) that maximizes difference between direction of travel of activated and non-activated neutrophils is determined.

To most closely match conditions in the final device, a microfluidic flow chamber with a channel height of 15 μm as in the proposed device design (described in Example 10) is used instead of the commercially available flow chamber for this set of experiments. Trajectories are obtained for activated and non-activated neutrophils rolling on arrangements for different values of $\alpha_s$ ranging from 5°, 10°, 20°, 30°, 40°, and 50°. Matlab analysis of cell tracks is carried out to determine (a) fraction of rolling cells that continue into free stream when they encounter an edge, (b) fraction of rolling cells that start following an edge, (c) path traveled by each cell while following an edge before detachment, and (d) velocity of rolling of each cell. These data can be easily extracted with a little modification to the Matlab program we are currently using. The net average deflection perpendicular to the flow direction that a rolling cell can undergo due to the P-selectin and anti-CD64 mAb arrangements is calculated as the average path length multiplied by sin($\alpha_s$). The edge angle ($\alpha_s$) that maximizes the difference between the rolling of activated and non-activated neutrophils is identified.

To verify that the difference in deflection is indeed due to CD64, control experiments using only P-selectin are performed. If the rolling behavior of activated and non-activated neutrophils is similar on P-selectin coated surfaces, the difference may be attributed to CD64 expression on the activated neutrophils. Furthermore, the number of non-activated and activated neutrophils that adhere to a surface coated only with anti-CD64 mAb is quantified. This is expected to confirm that the altered rolling behavior of the activated neutrophils is indeed due to CD64 expression.

Example 10

Microfluidic Device to Distinguish CD64$^+$ Activated Neutrophils from Non-Activated Neutrophils The present Example is directed to providing a device that can distinguish between activated and non-activated neutrophils.

After identifying receptor densities and arrangements that maximize difference between trajectories of activated and non-activated neutrophils, microfluidic devices to distinguish between the two cell states are fabricated. Studies of neutrophil CD64 expression have shown that CD64 expression of neutrophils exhibits a single Gaussian distribution; furthermore, CD64 expression increases several fold by a factor of 10 or more as entire distribution shifts during sepsis (Davis, B. H. et al. 2006. "Neutrophil CD64 is an improved indicator of infection of sepsis in emergency department patients." *Archives of Pathology & Laboratory Medicine*. 130(5): 654-661.). Therefore, a device that distinguishes between CD64$^+$ or CD64$^-$ neutrophils should be useful to detect conditions of sepsis.

For separation of cells using rolling, two major modifications to commercially available flow chambers would be advantageous. Commercially available flow chambers that are typically used in cell rolling studies (Hong et al. 2007) have heights in the range of about 125 μm or larger, which results in most cells just flowing through the chamber without ever encountering the receptor-coated surface or edge. Such flow chambers have only one inlet and one outlet, which is not useful for separation of cells.

In contemplated devices of the present Example, the height of the channels is decreased to about 15 μm to promote interaction between the cells and the surface. Furthermore, two inlets (cell and buffer) and two outlets is incorporated for separated cells. Decreasing the dimensions of the flow chamber may adversely affect the throughput of the device. On the other hand, the high density of neutrophils in blood requires analysis of very minute sample volumes and therefore likely avoids issues with throughput. In other applications where higher throughput is necessary, these devices could be manufactured to operate in parallel. Indeed, the technology to fabricate thousands of integrated chambers in a single device (Thorsen, T. et al. 2002. "Microfluidic large-scale integration." *Science*. 298(5593), 580-584, the contents of which are hereby incorporated by reference in their entirety) has already been commercialized (Fluidigm, Inc.) and is in routine use in several academic laboratories worldwide.

Device Design

Figure 20:
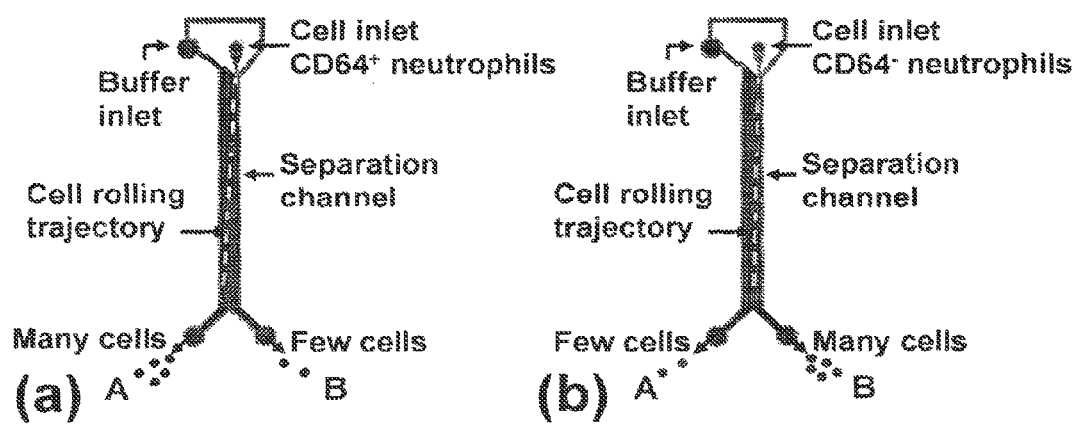
FIG. 20 shows a schematic for a device that could be used to sort activated CD64$^+$ neutrophils from non-activated (CD64$^-$) neutrophils. Activated neutrophils (A) are expected to be distinguishable from non-activated neutrophils (B) as they travel at a different angle and exit through outlet A. Non-activated neutrophils exit through outlet B. Activated neutrophils may be detected from a shift in the relative distribution of cells at the two outlets.

The device comprises an inlet for cell suspension, another inlet for buffer, a separation flow chamber, and two outlets (FIG. 20). The device is fabricated from PDMS (polydimethylsiloxane) (Sylgard 184, Dow Corning) using a standard micromolding process on a SU-8 (photocurable epoxy from Microchem, Inc.) (Duffy et al. 1998). If necessary, supporting posts or hard backing using a glass slide are used to prevent collapse of the microchannel. P-selectin and anti-CD64 mAb are immobilized separately on a glass slide using microfluidic patterning. The device will be assembled using a vacuum manifold to hold the PDMS component against the glass substrate with receptors.

Results from Example 9 are used to guide design of the device, for example, in terms of geometry, receptor densities, and edge angle. The cell suspension inlet width is kept to ~20 µm, since increasing this width increases the separation distance and thereby increases the time required for cells to flow through the device. It is anticipated that for deflection angles of the order of 10°, a flow chamber with length on the order of 1-10 mm may be needed for separation, giving cell flow-through time in the range of 1-10 min. For physiological shear stress of about 1 dyn/cm², the cell suspension inlet flow rate is slow, on the order of about 1 µL/minute. Nevertheless, with the very high density of neutrophils in blood, small amounts of blood (~1-10 µL) should be sufficient for collection and quantification of separated cells. Thus, a single device may be used to separate and quantify CD64⁺ neutrophils on a timescale of minutes.

Using a long separation chamber, the lateral distribution of the flux of cells at different positions along the separation channel is determined independently for CD64⁺ and CD64⁻ neutrophils under the same flow and surface design conditions. This information will facilitate designing the device outlets such that the CD64⁺ neutrophils are diverted selectively into outlet A, while CD64⁻ and non-rolling cells flow into outlet B (FIG. 20).

Cell Separation

Approximately 10 µL of neutrophil suspension at a density of 5×10⁴ cells/mL (typical of physiological density in blood) and buffer are flowed into the device at shear stress of 1 dyn/cm². Fractions of separated cells in each of the outlets are collected and quantified for relative distribution of cells in each outlet (FIG. 20). Volumes collected are measured using a pipette and added to 96 well plates. Cells are allowed to settle at the bottom of the well and manually counted under a microscope. For each separation experiment, the final output (c) is the relative ratio of the number of cells in outlet A ($n_A$) as compared to the number of cells in outlet B ($n_B$):

$$\varphi = \frac{n_A}{n_B} \quad \text{(Eq. 4)}$$

Separate experiments are performed for activated neutrophils (mimicking the sepsis condition) and non-activated neutrophils (normal condition). A significant difference in the relative distribution (φ) between activated and non-activated neutrophils indicates successful identification of activated neutrophils from non-activated neutrophils.

An objective criterion for V is established based on these preliminary results to distinguish between non-activated and activated cells as a cutoff ratio $\phi_C$. If $\phi < \phi_C$, then the result is FALSE for presence of CD64+ neutrophils, else it is TRUE. Several separation experiments (>10 each for activated and non-activated neutrophils) are then carried out with this objective criterion to quantify the specificity and sensitivity of the technique.

To determine the impact of CD64 site density on separation efficiency, we are treating primary human neutrophils with approximately 0.5 nM, 2 nM, or 5 nM TNF-α, determining their site density using the bead method described in Example 9, and determining separation efficiency described herein. This study is expected to yield the sensitivity of the device for various levels of CD64 expression on neutrophils.

Example 11

Development of Surfaces for Selective Rolling of HT29 Cells Along an Edge

In this Example, surfaces for separation of cancer cells from leukocytes are developed. Such cell rolling-mediated separation of cancer cells may be useful in diagnostic applications. HT29 is a well-established cell line that interacts with E-selectin and has been used as a circulating tumor cell model for metastasis. HL60 cells is a mycloid cell line that is used as a model for leukocyte cell rolling. This Example intends to demonstrate that HT29 cell can be selectively separated from HL60 cells using cell rolling based separation systems of the present invention.

Surfaces comprising edges between coated and uncoated areas are developed with coimmobolized E-selectin and epCAM Ab to enable separation of HT29 cells by rolling. Covalent chemistry is used to co-immobilize E-selectin and epCAM mAb (R&D Systems).

Covalent Immobilization of E-Selectin and epCAM mAb with Controlled Density on a Glass Substrate Epoxy chemistry is used to covalently immobilize the receptors on glass substrates. Epoxy-functionalized glass slides is obtained from ArrayIt Inc. and used directly for covalent immobilization without further treatment. E-selectin and epCAm mAb is arranged on surfaces using microfluidic patterning (Delamarche et al. 1997). In this technique, microfluidic channels in polydimethylsiloxane (PDMS) is reversibly bonded to the glass slide, and the desired receptor solution comprising an appropriate mixture of E-selectin and epCAM mAb is flowed through the microfluidic channel for immobilization. After immobilization, the PDMS component is peeled off and the entire surface is blocked with 5 mg/mL BSA for 1 hour.

Control of surface densities of E-selectin and epCAM mAb may be important for developing an optimized cell separation device. To test different densities of E-selectin and epCAM mAb, their concentrations are varied in the solution during microfluidic patterning. Initial experiments use different ratios of E-selectin:epCAM mAb concentrations of 1:1, 10:1, and 20:1 (with E-selectin concentrations kept at about 5 µg/mL). Surfaces are characterized for surface density of E-selectin and epCAM mAb using a radio-labeling technique as described below.

Site density is measured using radio-labeling with iodine ($^{125}$I) and using methods similar to those described in Example 8. Site density of epCAM expression in HT29 cells is quantified using flow cytometry as described in Example 9.

Characterization of HT29 and HL60 Rolling on Co-Immobilized Substrates

The effect of edges between E-selectin and epCAM mAb coated areas and uncoated on the rolling direction of HT29 and HL60 cells with respect to the direction of fluid flow is investigated. A goal of this study is to maximize the ability of the edges to direct trajectories of HT29 cells versus HL60 cells by varying E-selectin and epCAM mAb surface densities and edge angles. This study is expected to facilitate designing a device for cell separation and help determine relative sensitivities of the separation technique to neutrophil activation. Rolling experiments are performed in a microfluidic cell rolling devices we developed using PDMS microfabrication. The cells are flowed over the glass slide at shear stress of 1 dyn/cm$^2$, which is within the range of physiological shear stress. Images are acquired using a Nikon TE2000U microscope and analyzed using Matlab. Optimal surface densities of E-selectin and epCAM mAb are determined using methods similar to those described in Example 9.

Determining Edge Angle to Maximize Differences Between Trajectories of HT29 and HL60 Cells After identifying the E-selectin and epCAM mAb surface densities, the optimal edge angle ($\alpha_s$) to maximize separation of HT29 and HL60 cells is determined. A design comprising stripes of selectin/mAb defined by width of selectin strip (w) and angle with respect to flow direction ($\alpha_s$) (FIG. 5) is used. The width of selectin strips are fixed at w=10 μm (slightly larger than the adhesion area of a rolling cell) and the edge angle ($\alpha_s$) that maximizes difference between direction of travel of HT29 (circulating tumor cells) and HL60 (leukocytes) is determined.

Cell rolling trajectories are obtained for HT29 and HL60 cells using a microfluidic flow chamber as described in Examples 9 and 10.

Example 12

Microfluidic Device to Separate HT29 and HL60 Cells

In this Example, optimized surfaces for selective rolling of HT29 cells (developed in Example 11) are incorporated into microfluidic devices for separating HT29 cells from HL60 cells. Such devices may be modified for other cell separation devices that may have diagnostic applications. For example, they may be modified for separating and allowing detection of circulating tumor cells from blood or blood products. (See Example 13).

Device Design

Devices comprise an inlet for cell suspension, another inlet for buffer, a separation flow chamber, and two outlets (similar to the device schematic depicted in FIG. 20) fabricated from PDMS using a standard micromolding process (Duffy et al. 1998). If necessary, supporting posts or hard backing using a glass slide are used to prevent collapse of the microchannel. E-selectin and epCAM mAb are immobilized separately on glass slides using microfluidic patterning as described in Example 11. Devices are assembled using a vacuum manifold to hold PDMS components against the glass substrates with receptors.

Results from Example 11 are used to guide design of the device, for example, geometry, receptor densities, and edge angle. The cell suspension inlet width is kept to ~20 μm, since increasing this width increases the separation distance and thereby likely increases the time required for cells to flow through the device. It is anticipated that for deflection angles of the order of 100, a flow chamber with length of the order of 1-10 mm may be needed for separation, giving cell flow-through time in the range of 1-10 min. For physiological shear stress of about 10 dyn/cm$^2$, the cell suspension inlet flow rate is on the order of 1 μL/min. Using a long separation chamber, the lateral distribution of the flux of cells at different positions along the separation channel is determined independently for HT29 and HL60 cells under the same flow and surface arrangement conditions. This information will be used to design device outlets such that HT29 cells are diverted selectively into one outlet, while HL60 cells flow into the other outlet. (See FIG. 20 for a similar device schematic.)

Separation Throughput

A single device may, for example, be capable of cell separation at the rate of approximately 1 μL/min. Such a rate may be sufficient for initial development and testing of the device, but inadequate for processing of large sample volumes. Nevertheless, it is possible to construct multiple separation chambers that operate in parallel due to the inherent simplicity of the device geometry. With an estimated footprint of 10 mm$^2$, a single device could accommodate ~100 chambers in parallel enabling a throughput of 100 μL/min. (This throughput rate could scale up to multiple mL/min in a larger device). These devices can be fabricated in multilayer PDMS and attached to the same substrate with receptor arrangements.

Cell Separation

A cell suspension comprising HL60 cells at a density of 10$^5$ cells/mL (typical of physiological leukocyte density in blood) spiked with HT29 cells is flowed into the device at shear stress of 1 dyn/cm$^2$. HT29 cells are stained with calcein for subsequent analysis. Concentrations of HT29 cells are varied from 1 to 10$^3$ cells/mL to span the range of clinically relevant concentrations (Nagrath, S. et al. 2007. "Isolation of rare circulating tumor cells in cancer patients by microchip technology." *Nature.* 450 (7173):1235-U10, the entire contents of which are hereby incorporated by reference in their entirety). Fractions of separated cells in each of the outlets are collected and quantified for relative distribution of cells in each outlet by flow cytometry. Selectivity of the separation process is quantified as the fraction of HT29 cells in the separated sample. Yield is quantified as the fraction of HT29 cells that are separated compared to the total number of HT29 cells in the sample. Selectivity and yield are quantified as a function of the HT29 spiked concentration in the cell suspension.

Example 13

Separation of Circulating Tumor Cells (CTCs) from Whole Blood Samples of Cancer Patients In this Example, systems for separating circulating tumor cells (CTCs) from bodily fluids such as blood samples are developed, building on results from Examples 11-12.

Viable clinical samples of blood from late stage colon cancer patients with metastasis are obtained. Anticipated levels of CTC in such samples are high. Cell rolling experiments are performed on whole blood samples with epCAM and E-selectin co-immobilized substrates to separate CTCs from leukocytes without pre-labeling or processing of samples. Blood samples with a high fraction of CTCs are analyzed by flow cytometry (using a with a BD FACS Calibur flow cytometer) using epCAM mAb to quantify the density of CTCs in blood. Approximately 100 μL-1 mL of the same sample of blood (depending on device throughput)

are flowed through the device for separation using the same surface arrangements and flow conditions as in Example 12.

The resulting fractions are analyzed by flow cytometry to quantify the number of CTCs separated from blood. An iterative approach may be used to facilitate characterization of rolling CTCs, as rolling of CTCs cannot be directly characterized due to their small number compared to other cells. If separation is not obtained with the surfaces and flow rates obtained in Example 12, the edge angle is increased just beyond the angle at which CTCs can roll along the receptor edge. If CTCs are not detected under these conditions in the human blood samples, HT29 cells are spiked in blood and the lowest concentration at which they can be detected and separated are determined. To enhance the ability to track HT29 cell separation, HT29 cells are pre-labeled with CellTracker Green CMFDA (Molecular probes).

Example 14

Additional Arrangements for Use in Cell Separation Systems

In addition to the arrangements discussed in Example 6 and depicted in FIG. 3, a variety of other arrangements may be used to achieve cell separation. Some such arrangements are depicted in FIGS. 2 and 4. "Negative" selection of rolling cells may be achieved, for example, by using edges to divert undesired cells. (See, for example, FIG. 4A.) In such cell separation schemes, desired cell populations are not diverted by edges and move in the direction of fluid flow. Cells that are not desired roll along edges designed to induce rolling of the cell type(s) of the undesired cells.

Arrangements may be designed to separate cells into single files, which may be useful for certain downstream analyses and/or applications. (See, for example, FIG. 4B.) Alternatively or additionally, arrangements may incorporate elements designed to capture cells in certain locations on surfaces, as depicted in FIG. 4C. For example, elements may be physical structures that impede cells from flowing in the direction of flow. Such physical elements include microwells, which could be depressions in the surface where cells may become trapped. In some embodiments, patches of adhesive ligands (such as, for example, antibodies) that facilitate cell immobilization, etc. are used to trap cells. Arrangements may incorporate adhesive areas leading to edges to enable cells to roll before encountering the edge. (See, for example, FIG. 4D).

Net displacement of two cell types may be achieved by using arrangements comprising at least two edges that form different angles to the direction of flow. (See, for example, FIG. 2.) A first edge may make an angle such that both types of cells roll along it. A second edge may make a larger angle or have a different receptor composition such that only one cell type (whose trajectory is indicated by dashed lines in FIG. 2) can roll along that edge. The repeating pattern depicted in FIG. 2 can be spatially varied by changing, for example, the second edge gradually over a large area; such a change may facilitate separation of a particular cell type.

As illustrated by this Example and by other arrangements described herein, arrangements may have any of a diverse number of geometric designs and may or may not incorporate certain elements (such as, for example, microwells, patches of adhesive ligands, etc.) depending on the application.

Example 15

Three-Dimensional (3D) Devices for Cell Separation

In this Example, three-dimensional (3D) devices for cell separation will be provided. As discussed and exemplified herein, in two-dimensional systems of the invention, an edge between areas coated with cell adhesion molecules (such as, for example, P-selectin and/or E-selectin) and uncoated areas facilitates cell rolling. Cells roll along the edge and are directed along a particular direction at an angle to the direction of fluid flow.

Figure 21:
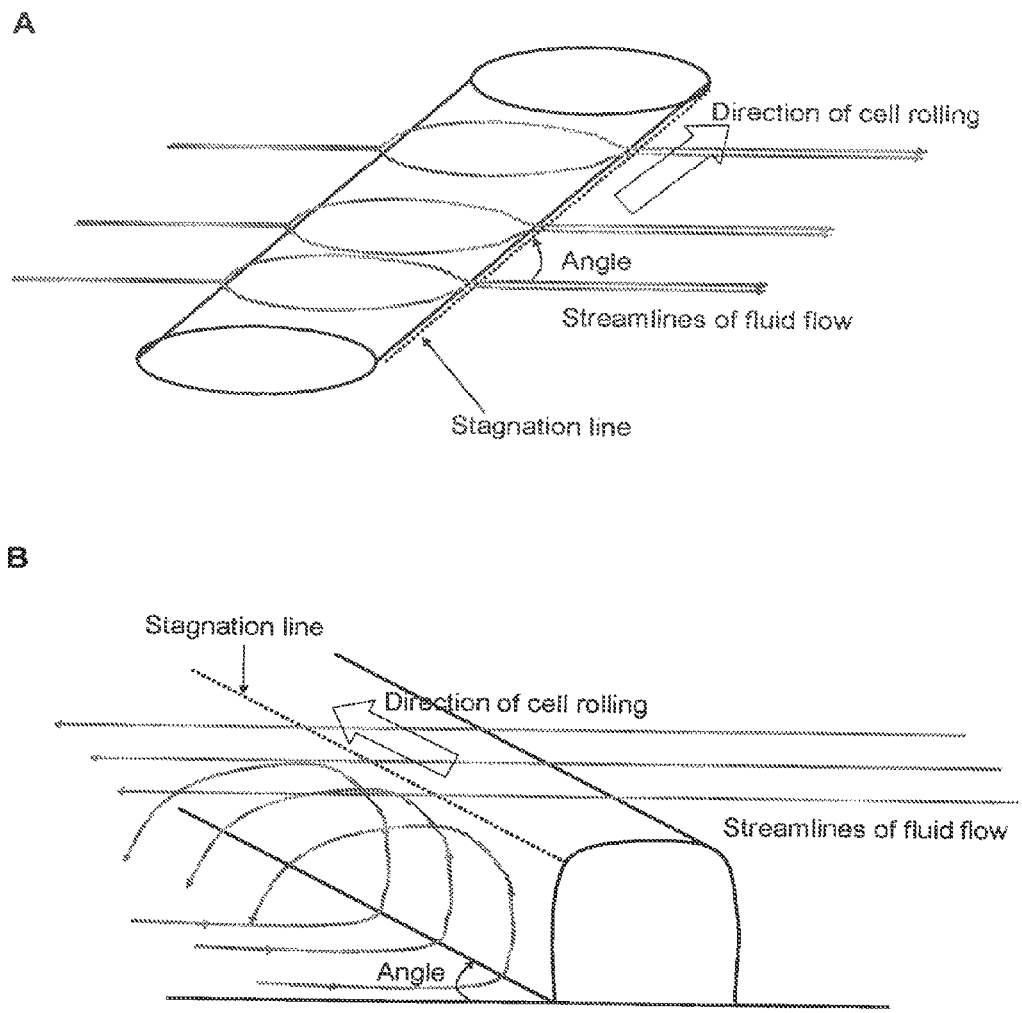
FIG. 21 shows examples of surfaces that can be used to create stagnation lines for three-dimensional cell separation applications. (A) A cylinder and (B) a ridge can be coated on their outer surfaces with cell adhesion molecules and used in three-dimensional cell rolling-based separation systems. Arrows indicate streamlines of fluid flow. Stagnation lines represent regions of no flow in the near vicinity of the surface.

On three-dimensional surfaces, an effect similar to the edge effect can occur. A schematic of a three-dimensional device is depicted in FIG. 21. Streamlines indicating fluid flow are depicted by arrows. When flowing fluid encounters an object such as, for example, a cylinder (FIG. 21A) or a ridge (FIG. 21B), a "stagnation line" can be created. In such 3D devices, the stagnation line can act as a edge and facilitate cell rolling as explained below.

A stagnation line as defined herein is a region of zero flow velocity near a surface of an object where flows on the surface converge from different directions. The shear along the stagnation line is zero, and the flow velocity close to the surface defines a plane passing through the stagnation line. In this plane, the flow velocity must make an angle other than 90 degrees with respect to the stagnation line. The angle is 90 degrees in the case of vertical posts).

In contemplated 3D devices of the invention, exterior surfaces are coated with cell adhesion molecules that may induce cell rolling. Cells in the fluid flowing across the surface may be induced to roll on the surface. A cell rolling on the surface will roll towards the stagnation point, and then (under certain conditions) roll along the stagnation line and thereby follow it. Cells may roll in a direction at an angle to the direction of fluid flow when the stagnation line is at an angle to th direction of fluid flow. As in the case of rolling along a edge, cells may follow the stagnation line so long as the angle does not exceed a maximum angle $\alpha_{tr}$, whose value depends on the particular conditions of the cell separation system. The stagnation line may be curved depending on the surface under consideration and the flow field around the surface.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

We claim:
1. A device comprising:
a separation flow chamber, wherein the separation flow chamber comprises a surface that is at least partially coated with an ordered layer of cell adhesion molecules, and the surface comprises at least one edge between an area coated with the ordered layer and another area that is not coated with the ordered layer;
an inlet for flowing cells into the separation flow chamber;
an outlet for flowing cells out of the separation flow chamber;
a plurality of channels for collection of subpopulations of cells flowed through the separation chamber; and at least one porous filter situated at the end of at least one of the channels or between sequential channels;

wherein when cells are flowed through the inlet to the outlet they flow at an angle $\alpha_s$ to the direction of the at least one edge unless they interact with the at least one edge.

2. The device of claim 1, further comprising at least one additional outlet, at least on additional inlet, or combinations thereof connected to the separation flow chamber.

3. The device of claim 2, wherein at least one inlet introduces a population of cells into the separation flow chamber and at least one inlet introduces a buffer free of cells into the separation flow chamber.

4. The device of claim 1, wherein the separation flow chamber is defined by walls having a height between about 5 μm and 1 mm.

5. The device of claim 1, wherein the subpopulation of cells comprises stem cells.

6. The device of claim 1, further comprising a means for controlling flow rate.

7. The device of claim 6, wherein the means for controlling flow rate comprises a syringe pump.

8. The device of claim 5, wherein estimates of the numbers of collected cells can be obtained without further processing.

9. The device of claim 1, wherein cells are flowed in a fluid.

10. The device of claim 1, wherein the separation flow chamber comprises a plurality of three dimensional surfaces that are at least partially covered with an ordered layer of cell adhesion molecules.

11. The device of claim 10, further comprising a buffer inlet configured for flowing a buffer stream that does not contain cells.

12. The device of claim 10, wherein the plurality of three dimensional surfaces are defined by shapes selected from squares, rectangles, triangles, polygons, ellipses, circles, arcs, waves, and any combination thereof.

13. The device of claim 10, wherein the surfaces comprise at least one edge between an area coated with the ordered layer of cell adhesion molecules and another area that is not coated with the ordered layer.

14. The device of claim 1, wherein the cell adhesion molecules further comprises molecules that interact with a surface moiety present on at least one cell in a population of cells.

15. The device of claim 1, wherein the cell adhesion molecules are selected from the group consisting of selectins, integrins, cadherins, immunoglobulin cell adhesion molecules, and combinations thereof.

16. A device comprising:
a separation flow chamber, wherein the separation flow chamber comprises a surface that is at least partially coated with an ordered layer of cell adhesion molecules, and the surface comprises at least one edge between an area coated with the ordered layer and another area that is not coated with the ordered layer;
an inlet for flowing cells into the separation flow chamber;
an outlet for flowing cells out of the separation flow chamber; and
markings along a collection channel such that the height of a column of collected cells gives an indication of the cell volume and/or of the cell count;
wherein when cells are flowed through the inlet to the outlet they flow at an angle $\alpha_s$ to the direction of the at least one edge unless they interact with the at least one edge.

17. The device of claim 16, further comprising at least one additional outlet, at least on additional inlet, or combinations thereof connected to the separation flow chamber.

18. The device of claim 17, wherein at least one inlet introduces a population of cells into the separation flow chamber and at least one inlet introduces a buffer free of cells into the separation flow chamber.

19. The device of claim 16, wherein the separation flow chamber is defined by walls having a height between about 5 μm and 1 mm.

20. The device of claim 16, further comprising a means for controlling flow rate.

21. The device of claim 16, wherein cells are flowed in a fluid.

22. The device of claim 16, further comprising a buffer inlet configured for flowing a buffer stream that does not contain cells.

23. The device of claim 16, wherein the separation flow chamber comprises a plurality of three dimensional surfaces that are at least partially covered with an ordered layer of cell adhesion molecules.

24. The device of claim 22, wherein the plurality of three dimensional surfaces are defined by shapes selected from squares, rectangles, triangles, polygons, ellipses, circles, arcs, waves, and any combination thereof.

* * * * *